(12) United States Patent
Takigawa et al.

(10) Patent No.: US 9,887,514 B2
(45) Date of Patent: Feb. 6, 2018

(54) LASER APPARATUS ENABLING CALCULATION OF EFFECTIVE DRIVING TIME AND REMAINING LIFETIME TAKING ACCOUNT OF DRIVE CONDITIONS INCLUDING TEMPERATURE

(71) Applicant: FANUC CORPORATION, Yamanashi (JP)

(72) Inventors: Hiroshi Takigawa, Yamanashi (JP); Satoshi Kagiwada, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 0 days.

(21) Appl. No.: 15/640,728

(22) Filed: Jul. 3, 2017

(65) Prior Publication Data

US 2018/0013259 A1 Jan. 11, 2018

(30) Foreign Application Priority Data

Jul. 8, 2016 (JP) .................................. 2016-136319

(51) Int. Cl.

| | |
|---|---|
| *G01N 21/00* | (2006.01) |
| *H01S 5/00* | (2006.01) |
| *H01S 5/062* | (2006.01) |
| *G01N 21/68* | (2006.01) |
| *G01N 21/64* | (2006.01) |
| *G01J 3/02* | (2006.01) |

(52) U.S. Cl.
CPC ............ *H01S 5/0021* (2013.01); *H01S 5/062* (2013.01); *G01J 3/02* (2013.01); *G01N 21/64* (2013.01); *G01N 21/68* (2013.01)

(58) Field of Classification Search
CPC ...... H01S 5/00; H01S 5/062; H01J 37/32935; G01N 21/64; G01N 21/68; G01N 2015/1037; G01J 3/02
See application file for complete search history.

(56) References Cited

U.S. PATENT DOCUMENTS

| | | | |
|---|---|---|---|
| 2004/0150594 A1 | 8/2004 | Koyama et al. | |
| 2012/0051385 A1* | 3/2012 | Nishimura | .............. F04D 19/00 |
| | | | 372/58 |

FOREIGN PATENT DOCUMENTS

| | | |
|---|---|---|
| JP | 2003-173559 A | 6/2003 |
| JP | 2004-070349 A | 3/2004 |
| JP | 2004-335030 A | 11/2004 |
| JP | 2005-243089 A | 9/2005 |
| JP | 2014-212234 A | 11/2014 |

* cited by examiner

*Primary Examiner* — Abdullahi Nur
(74) *Attorney, Agent, or Firm* — Studebaker & Brackett PC

(57) ABSTRACT

A first calculation unit calculates an acceleration factor of lifetime consumption of the light source with as case of a standard temperature and standard drive condition as a reference, a second calculation unit calculates a whole lifetime or remaining lifetime of individual light sources relative to a performance index of the individual light sources or a change rate of the performance index, a computation unit obtains an effective cumulative driving time at which the magnitude of influence imparted on the lifetime is equivalent with a case of driving at the standard temperature and standard drive condition, by calculating a time integral of the acceleration factor, and a recording unit records the effective cumulative driving time and the whole lifetime or remaining lifetime together with an optical output characteristic of the light source.

15 Claims, 16 Drawing Sheets

FIG. 2
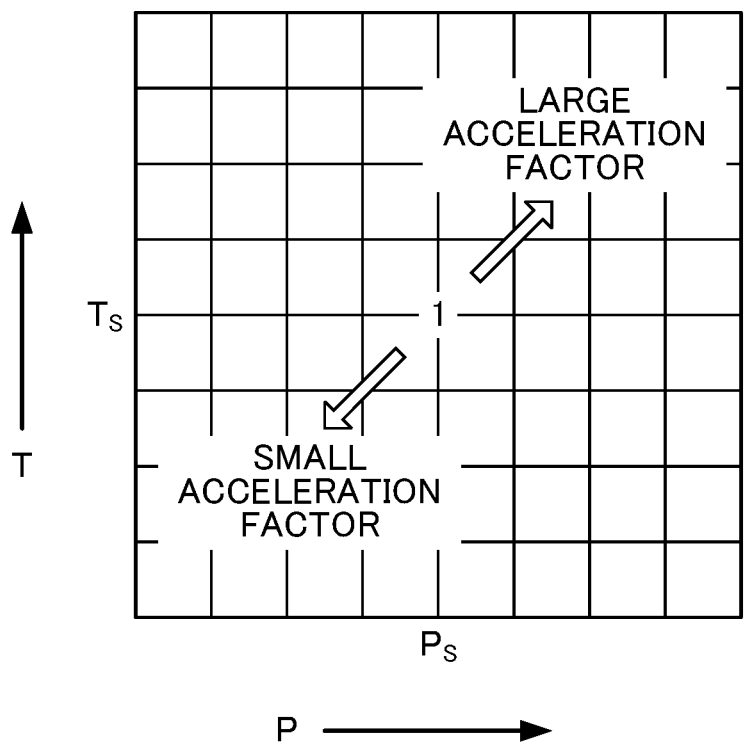
FIG. 3
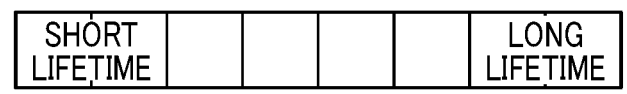

FIG. 10

| | | |
|---|---|---|
| $t = t_s$, | $t_c = 0$ | : OPTICAL OUTPUT CHARACTERISTIC$_0$ : $T_0$ : $Q_0$ : WHOLE LIFETIME = REMAINING LIFETIME$_0$ |
| | | : TRANSITION OF DRIVE CONDITION VALUE$_{0-1}$ : TRANSITION OF DETECTED TEMPERATURE$_{0-1}$ |
| $t = t_1$, | $t_c = t_{c1}$ | : OPTICAL OUTPUT CHARACTERISTIC$_1$ : $T_1$ : $Q_1$ : $\Delta Q/\Delta t$ : REMAINING LIFETIME$_1$ |
| | | : TRANSITION OF DRIVE CONDITION VALUE$_{1-2}$ : TRANSITION OF DETECTED TEMPERATURE$_{1-2}$ |
| $t = t_2$, | $t_c = t_{c2}$ | : OPTICAL OUTPUT CHARACTERISTIC$_2$ : $T_2$ : $Q_2$ : $\Delta Q/\Delta t$ : REMAINING LIFETIME$_2$ |
| | | : TRANSITION OF DRIVE CONDITION VALUE$_{2-3}$ : TRANSITION OF DETECTED TEMPERATURE$_{2-3}$ |
| $t = t_3$, | $t_c = t_{c3}$ | : OPTICAL OUTPUT CHARACTERISTIC$_3$ : $T_3$ : $Q_3$ : $\Delta Q/\Delta t$ : REMAINING LIFETIME$_3$ |
| | | : TRANSITION OF DRIVE CONDITION VALUE$_{3-4}$ : TRANSITION OF DETECTED TEMPERATURE$_{3-4}$ |
| $t = t_4$, | $t_c = t_{c4}$ | : OPTICAL OUTPUT CHARACTERISTIC$_4$ : $T_4$ : $Q_4$ : $\Delta Q/\Delta t$ : REMAINING LIFETIME$_4$ |
| | | : TRANSITION OF DRIVE CONDITION VALUE$_{4-5}$ : TRANSITION OF DETECTED TEMPERATURE$_{4-5}$ |
| $t = t_5$, | $t_c = t_{c5}$ | : OPTICAL OUTPUT CHARACTERISTIC$_5$ : $T_5$ : $Q_5$ : $\Delta Q/\Delta t$ : REMAINING LIFETIME$_5$ |
| ... | | |

LASER APPARATUS ENABLING CALCULATION OF EFFECTIVE DRIVING TIME AND REMAINING LIFETIME TAKING ACCOUNT OF DRIVE CONDITIONS INCLUDING TEMPERATURE

This application is based on and claims the benefit of priority from Japanese Patent Application No. 2016-136319, filed on 8 Jul. 2016, the content of which is incorporated herein by reference.

BACKGROUND OF THE INVENTION

Field of the Invention

The present invention is a laser apparatus including a light source which is used as a laser light source or an excitation light source for laser oscillation, which is a laser apparatus that can accurately calculate an effective driving time for which the magnitude of the influence imparted on the lifetime of the light source is equivalent in a case of driving so that the temperature of the light source is the standard temperature and the optical output is a standard optical output, or a case of driving with the driving current of the light source at a standard driving current, even if the temperature of the light source changes, and even if the optical output from the light source or the magnitude of the driving current of the light source changes, the laser apparatus being able to accurately calculate the accumulation of effective driving time since the moment starting counting of lifetime, i.e. the remaining lifetime by deducting the effective cumulative driving time from an estimated whole lifetime of the light source, and is capable of displaying or outputting the effective cumulative driving time and remaining lifetime as necessary.

Although the temperature variation of a light source is relatively small in a laser apparatus which water-cools the light source, in a laser apparatus which air-cools the light source, the temperature of the light source varies considerably from the influence of environmental temperature. Therefore, in a laser apparatus which is air-cooling the light source in particular, it is not possible to ignore the difference in the rate of lifetime consumption due to the temperature of the light source, similarly to the difference in rate of lifetime consumption due to the differences in magnitude of optical output and driving current. Therefore, it is necessary for effective driving time to be calculatable taking account of the influences on lifetime consumption of both temperature and the optical output or driving current.

The effective cumulative driving time is important information relevant to the warranty or maintenance of the light source. In addition, when the remaining lifetime enters the late stage of lifetime of the light source in particular, it is necessitated to accurately know the remaining lifetime for preparing a light source to replace or measuring the timing of light source replacement; however, there are individual variations in the lifetime of the light sources in addition, and thus it has be difficult to accurately estimate.

An object of the present invention is to provide a laser apparatus which can always calculate accurately the effective cumulative driving time of the light source, even in a case of driving the light source being used in the laser apparatus at conditions at which the temperature of the light source differs, and in a case of driving at various optical output conditions, and which can always calculate accurately the remaining lifetime of the light source by taking account of the individual variations between light sources by referencing cumulative data, even in the case of there being individual variations between the light sources, and which can display or output the effective cumulative driving time and remaining lifetime as required.

The laser apparatus described in the present disclosure is used as a laser beam machine mainly for sheet-metal cutting or welding, in the field of machining.

Related Art

Conventionally, a method for measuring the effective cumulative driving time or remaining lifetime of a light source or the like of a laser apparatus have been described in several publications as mentioned below; however, a publication has not been disclosed that calculates the effective driving time or effective cumulative driving time accurately by taking into consideration both an acceleration factor on the life consumption by the temperature of the light source and an acceleration factor on the life consumption by drive conditions such as optical output and driving current. In addition, for the remaining lifetime estimated as a time subtracting the effective cumulative driving time from the estimated whole lifetime, the originally accurate estimation is difficult when the effective cumulative driving time is not calculated accurately; thereby, there is no publication disclosing a method of accurately estimating the remaining lifetime by taking account of individual variation in light sources based on the characteristics or the change rate of the characteristic of the light source at the moment when a predetermined effective cumulative driving time elapses. In addition, although it goes without saying, since the change rate of characteristic is calculated by dividing the variation range of the characteristic by the effective driving time, unless an accurate effective driving time can be calculated, an accurate change rate of the characteristic cannot be obtained.

For example, Japanese Unexamined Patent Application, Publication No. 2004-335030 discloses technology that measures the temperature of a semiconductor laser and operation time, corrects the operation time by a temperature correction factor corresponding to the temperature at the time as necessary, cumulatively counts the operation time or corrected operation time, compares the counted cumulative operation time with a predetermined threshold, and displays a message as to whether to inhibit recording of data and establish as read only on a display unit when the cumulative operation time exceeds the threshold; however, there is no mention of correction on the optical output or driving current. In addition, the estimation accuracy of the remaining lifetime is low due to not taking consideration of the individual variation in semiconductor lasers.

In addition, Japanese Unexamined Patent Application, Publication No. 2014-212234 discloses technology that calculates, from the current value and the operation time of laser diode, the variation in bias current relative to the operation time thereof, and predicts the lifetime of the light emitter based on the variation thereof, and discloses technology that compares, based on the ambient temperature of the light emitter, the current value of the driving current at a predetermined operation time with a current value stored in association with the ambient temperature of the light emitter, and calculates the variation in bias current relative to the operation time thereof; however, there is no mention of an effective cumulative driving time taking consideration of the temperature and driving current. In addition, the estimation accuracy of the remaining lifetime is low due to not taking consideration of the individual variation of laser diodes.

Although Japanese Unexamined Patent Application, Publication No. 2005-243089 discloses technology that derives a weighting coefficient for correcting the influence on the lifetime of the usage environment temperature and accumulates the corrected driving time for an electronic device such as a semiconductor laser, even if the usage environment temperature is the same, the lifetime of the semiconductor laser greatly changes according to the optical output or driving current, including the matter of the temperature of a pn junction changing in the case of a semiconductor laser according to the driving current, etc.; however, only the influence of the actual usage environment temperature is corrected. Therefore, in a case of the driving current or optical output not being stable, correction is not possible, and accurate effective cumulative driving time is not possible; therefore, including the fact that the individual variation in semiconductor lasers is not taken into account, an accurate remaining lifetime cannot be estimated.

Japanese Unexamined Patent Application, Publication No. 2003-173559 discloses technology that measures the peripheral temperature and operation time of a light pickup of disk playback equipment, computes a damage index arrived at by multiplying a first parameter that increases accompanying a rise in temperature, and a second parameter that increases accompanying the elapse of operation time, using the measured peripheral temperature and operation time, and records an accumulated value of damage indices arrived at by accumulating the computed damage indices; however, there is no mention of differences in the size of damage in the case of the drive condition other than peripheral temperature differing, and in the case of the driving current, etc. not being stable, an accurate effective cumulative driving time cannot be calculated. Therefore, including the fact that the individual variation in light pickups is not taken into consideration, it is not possible to estimate an accurate remaining lifetime.

Japanese Unexamined Patent Application, Publication No. 2004-070349 discloses, with regard to a display panel to which pixels including light emitters are equipped, technology that stores the temperature characteristic of a light emitter and time-dependent change characteristic, calculates a lighting period of each pixel using the temperature around the light emitter, temperature characteristic of the light emitter and video signal, obtains a cumulative lighting period of each pixel, and corrects the video image inputted to each pixel using the time-dependent change characteristic of the light emitter and the cumulative lighting period of each pixel and supplies to a display panel. However, since it only obtains the cumulative lighting period by calculating the product of the acceleration factor and data of the lighting period of each pixel provided from a video signal, and nonetheless makes no mention of an acceleration factor in the case of driving current (supply current) differing, the accuracy is not desirable even when applying to a device requiring to variously change drive conditions such as the optical output and driving current as in a laser apparatus for laser machining.

Patent Document 1: Japanese Unexamined Patent Application, Publication No. 2004-335030
Patent Document 2: Japanese Unexamined Patent Application, Publication No. 2014-212234
Patent Document 3: Japanese Unexamined Patent Application, Publication No. 2005-243089
Patent Document 4: Japanese Unexamined Patent Application, Publication No. 2003-173559
Patent Document 5: Japanese Unexamined Patent Application, Publication No. 2004-070349

SUMMARY OF THE INVENTION

For a light source that is an essential component of a laser apparatus, the effective cumulative driving time and remaining lifetime are important information from the viewpoint of warranty and maintenance. If the effective cumulative driving time is not known, for example, problems arise such as the characteristic of the light source degrading, and when the lifetime has exhausted, it is not known from the average light source whether degradation is fast or the lifetime is short, and it is not possible to feed back to the reliability control of the light source, and to judge the lifetime from the viewpoint of lifetime assurance. In addition, if the accurate remaining lifetime is not known, problems occur such as preparation for replacement of the light source being delayed, and disorder arising in the production schedule for maintenance work.

If configuring to be driven so that the temperature of the light source is constant, and the light source outputs only a constant standard optical output, or only a constant standard driving current is applied to the light source, although it is easy to obtain the cumulative driving time, in the case of a laser apparatus for laser machining or the like, it is often used in practice at various optical output conditions from low output to high output, and from continuous laser output to pulse laser beam output. In addition, although keeping the temperature condition of the light source almost constant is relatively easy in the case of the light source being water cooled, in the case of being air-cooled, which has merits in the point of portability or weight, size, etc., it is difficult to avoid the temperature condition of the light source from changing by the influence of the environmental temperature. For this reason, the drive conditions such as optical output and driving current, or temperature condition of the light source are not necessarily constant, and it has been necessary to accurately calculate the effective driving time and effective cumulative driving time which is the cumulative value thereof, which are equivalent to the driving time and lifetime consumption of the light source driven at the standard drive conditions and standard temperature condition; however, with the conventional technology, for the light source of the laser apparatus for which the drive conditions including the temperature of the light source are not constant, it has not been possible to calculate an accurate effective driving time or effective cumulative driving time.

In addition, it is desirable to be able to grasp the remaining lifetime also at the lifetime early stage prior to degradation of the light source starting from the purpose such as ensuring the estimate by advanced anticipation of the replacement period of the light source, and when entering the lifetime late stage of the light source, it is demanded to specifically know with accuracy the remaining lifetime for preparing a replacement light source and measuring the timing of light source replacement.

However, with the conventional technology, for the light source of a laser apparatus for which the drive conditions including the temperature of the light source are not constant, it may not be possible to calculate the originally accurate effective cumulative driving time, and for the light source driven at such conditions, it has not been possible to estimate the remaining lifetime if degradation has not manifested. Furthermore, there is individual variation in the degradation rate of the characteristic of light sources, and moreover, degradation rate varies along with the elapse of effective cumulative driving time, and thus the matter of there being individual variation also in the way of change thereof makes accurate estimation of the remaining lifetime increasingly difficult.

As mentioned above, it is problem to develop a laser apparatus that, even when using by variously changing the drive conditions including the temperature of the light source, can always calculate an accurate effective cumulative driving time of the light source, can always accurately derive the remaining lifetime, by considering the individual variation of the light source within the lifetime period from the lifetime early stage of the light source at which degradation of the light source has not manifested until the lifetime late stage at which the influence of degradation on the light source has become remarkable, and can derive a higher accuracy remaining lifetime particularly for the lifetime late stage which requires accuracy in the remaining lifetime.

A first aspect of the present invention provides a laser apparatus including: at least one light source that functions as a laser beam source or excitation light source; at least one power supply unit that supplies driving current to the light source; at least one optical output detection unit that detects optical output from the light source; at least one temperature detection unit that detects temperature of the light source or a member that is thermally connected with the light source; a first calculation unit that defines, as a standard, a case of a temperature detected by the temperature detection unit or the temperature of the light source obtained from the temperature detected by the temperature detection unit being a standard temperature, and optical output from the light source or at least one drive condition value of the light source deciding the optical output being a standard condition value, and calculates an acceleration factor of life consumption of the light source which depends on the temperature and the drive condition value; a second calculation unit that calculates at least one lifetime among a whole lifetime of the light source and a remaining lifetime of the light source relative to at least one characteristic of the light source, among at least one performance index of the light source that changes accompanying driving of the light source and can be obtained from an optical output characteristic of the light source, and a change rate of the performance index; a computation unit that computes a time integral of the acceleration factor as an effective driving time of the light source; a recording unit that records the time integral of the acceleration factor from a certain setting time that was set until an arbitrary time that is later than the setting time, which was computed by the computation unit, as an effective cumulative driving time until the arbitrary time, and can record the whole lifetime and the remaining lifetime calculated by the second calculation unit with the optical output characteristic; and a control unit that controls each of the units.

According to the laser apparatus as described in the first aspect, even if the drive conditions such as the temperature of the light source and the optical output or driving current change, since the effective driving time converted to the driving time for the case of driving the light source at the standard temperature and the standard drive condition value, and effective cumulative driving time can be calculated, it comes to be possible to quantitatively evaluate the lifetime or reliability of the light source. In addition, it is possible to estimate with high accuracy the whole lifetime or remaining lifetime of the light source due to calculating the whole lifetime or remaining lifetime of the light source by considering the characteristic individual variations in the performance index of the light source or change rate of the performance index. Furthermore, since it is possible to record the calculated whole lifetime or remaining lifetime, and optical output characteristic of the light source, along with recording the effective cumulative driving time, in a case of leaving the whole lifetime or remaining lifetime, or optical output characteristic in the recording, it is possible to verify the calculation accuracy of the first calculation unit or second calculation unit, and thus it is possible to use as information for further improving the calculation accuracy.

According to a second aspect of the present invention, in the laser apparatus as described in the first aspect, the dependency on the effective cumulative driving time may be considered in the acceleration factor calculated by the first calculation unit.

According to the laser apparatus as described in the second aspect, when reaching the lifetime late stage, for the acceleration factor F (P,T) larger than 1 being the reference value, even if the drive condition value P and temperature T are the same, there is a tendency for the acceleration factor F (P,T) to gradually increase; however, even in the case of the acceleration factor differing according to the effective cumulative driving time, an accurate effective driving time or effective cumulative driving time can be calculated.

According to a third aspect of the present invention, in the laser apparatus as described in the first or second aspect, the remaining lifetime of the light source may be calculated by the second calculation unit subtracting the effective cumulative driving time until the arbitrary time recorded in the recording unit from a whole lifetime of the light source calculated relative to at least one characteristic of the light source among the performance index of the light source and a change rate of the performance index.

According to the laser apparatus as described in the third aspect, the second calculation unit can calculate the remaining lifetime by subtracting the effective cumulative driving time from the whole lifetime of the light source calculated from the initial characteristic of the performance index, e.g., performance index at the setting time. In this case, since the individual variations in light sources such as the initial characteristic of the performance index is being taken into consideration, an accurate remaining lifetime can be calculated. In addition, an accurate remaining lifetime can be calculated from the lifetime initial stage prior to characteristic degradation of the light source manifesting.

According to a fourth aspect of the present invention, in the laser apparatus as described in any one of the first to third aspects, the power supply unit may output driving current for optical output measurement to the light source according to a command from the control unit following a predetermined schedule, the control unit may measure an optical output characteristic of the light source expressing a relationship between the driving current and optical output detected by the optical output detection unit, and the recording unit may add or record the optical output characteristic in the recording unit to be associated with the effective cumulative driving time at a corresponding time.

According to the laser apparatus as described in the fourth aspect, by adding or recording the optical output characteristic in the recording unit to be associated with the effective cumulative driving time, for the performance index that can be obtained from the optical output characteristic, it is possible to know the variation range, and since the change rate of the performance index is obtained by dividing the variation range by the difference in effective cumulative driving time, a remaining lifetime that takes into account the individual variation including the degradation rate in characteristic of the light source comes to be calculatable.

In addition, by performing by adding the optical output characteristic, it is possible to leave a history of the optical output characteristic and change in performance index accompanying the elapse of effective cumulative driving time, and thus it is possible to use as information for further improving the calculation accuracy of the first calculation unit and second calculation unit. By updating the optical output characteristic of the light source obtained from the optical output detected by changing the driving current, there is an effect of accurate optical output relative to the optical output command becoming possible.

According to a fifth aspect of the present invention, the laser apparatus as described in any one of the first to fourth aspects may include a plurality of the light sources for which the driving current is independently controllable, and may include at least one of the optical output detection units capable of detecting optical output relative to each of the light sources for which the driving current is independently controllable.

According to the laser apparatus as described in the fifth aspect, since it is possible to simultaneously measure the optical output characteristic of a plurality of light sources, the optical output characteristic can be measured in a short time.

According to a sixth aspect of the present invention, in the laser apparatus as described in any one of the first to fifth aspects, the dependency on the effective cumulative driving time may also be considered in the remaining lifetime of the light source calculated by the second calculation unit relative to a performance index of the light source and the change rate of the performance index.

According to the laser apparatus as described in the sixth aspect, for example, even with the same performance index and the change rate of the performance index, for a light source having a short effective cumulative driving time, it means that degradation started from early on, and there are more degradation factors than usual; therefore, from thereon the degradation advances rapidly and the remaining lifetime is estimated as short. Therefore, calculation of a higher accuracy remaining lifetime becomes possible by calculating the remaining lifetime by also taking consideration of the effective cumulative driving time in addition to the performance index of the light source and the change rate of the performance index.

According to a seventh aspect of the present invention, in the laser apparatus as described in any one of the first to sixth aspects, in a case of the change rate or a variation range of the performance index obtained from the optical output characteristic recorded or added in the recording unit to be associated with the effective cumulative driving time exceeding a predetermined value that exceeds measurement error for the optical output characteristic, the whole lifetime calculated by the second calculation unit based on the performance index of the light source or the change rate of the performance index may be replaced with a value arrived at by adding the effective cumulative driving time to the remaining lifetime of the light source calculated from the performance index of the light source obtained from the optical output characteristic of the light source newly measured and the change rate of the performance index.

According to the laser apparatus as described in the seventh aspect, when characteristic degradation of the light source, i.e. change in performance index, manifests, since the remaining lifetime directly calculated from the most recent performance index of the light source and change rate of the performance index is higher accuracy than the remaining lifetime obtained by subtracting the effective cumulative driving time from the whole lifetime calculated in the past, it is possible to update to a high accuracy whole lifetime.

According to an eighth aspect of the present invention, in the laser apparatus as described in any one of the first to seventh aspects, the recording unit may record or add the remaining lifetime of the light source at the effective cumulative driving time, calculated by the second calculation unit, along with the optical output characteristic recorded or added to be associated with the effective cumulative driving time, in the recording unit.

According to the laser apparatus as described in the eighth aspect, the accuracy of the remaining lifetime calculated from the performance index calculated from the optical output or the change rate of the performance index can be verified at the moment at which the lifetime is exhausted, by leaving history of the optical output relative to the elapse of effective cumulative driving time and the remaining lifetime calculated by the second calculation unit. Furthermore, it is possible to use as information for improving the calculation accuracy of the first calculation unit or second calculation unit.

According to a ninth aspect of the present invention, in the laser apparatus as described in any one of the first to eighth aspects, the recording unit may have a function of recording or adding information related to at least one drive condition of the light source among a temperature detected by the temperature detection unit or the temperature of the light source obtained from the temperature detected by the temperature detection unit, and the drive condition value of the light source, over a time period from a measurement time of the optical output characteristic until a subsequent measurement time of the optical output characteristic, together with the optical output characteristic recorded or added to be associated with the effective cumulative driving time in the recording unit.

According to the laser apparatus as described in the ninth aspect, since information related to drive conditions of the light source from a measurement time of the optical output characteristic until a subsequent measurement of the optical output characteristic is recorded, it is possible to verify that the acceleration factor relative to the drive condition during this time is not an overestimation or underestimation, and it is possible to use as information for improving the calculation accuracy of the first calculation unit. If the calculation accuracy of the first calculation unit improves, since the calculation accuracy of the effective cumulative driving time improves, it is possible to also improve the calculation accuracy of the second calculation unit.

According to a tenth aspect of the present invention, in the laser apparatus as described in any one of the first to ninth aspects, it may be configured to be able to output data recorded in the recording unit by a recording medium or by a communication means.

According to the laser apparatus as described in the tenth aspect, by collecting history data recorded in the recording unit, also including the effective cumulative driving time at the moment at which the lifetime of the light source actually is exhausted, it is possible to compare the whole lifetime or remaining lifetime calculated by the first calculation unit or second calculation unit with the actual whole lifetime or remaining lifetime, and thus it is possible to revise and update the reference data referenced by the first calculation unit or second calculation unit upon calculation so that the difference therebetween decreases. As a result thereof, it is possible to further improve the calculation accuracy of the effective cumulative driving time, whole lifetime and remaining lifetime.

According to an eleventh aspect of the present invention, in the laser apparatus as described in any one of the first to tenth aspects, since it is desirable for the data referenced by the first calculation unit or second calculation unit upon calculating to be the latest version of data, at least one set of data among data referenced by the first calculation unit upon calculation of the acceleration factor and data referenced by the second calculation unit upon calculating the whole lifetime or the remaining lifetime of the light source can be substituted for data by way of a recording medium or communication means, at a moment at which the effective cumulative driving time of the laser apparatus elapses, and a recording may be left in the recording unit of at which moment of the effective cumulative driving time the data to be referenced was substituted, so that data recorded in the recording unit can be analyzed.

According to the laser apparatus as described in the eleventh aspect, by replacing data referenced by the first calculation unit or second calculation unit upon calculation with the latest version, it is possible to improve the calculation accuracy of the effective cumulative driving time, whole lifetime, and remaining lifetime thereafter. By leaving as a recording which version of the data was referenced to perform calculation of the effective cumulative driving time, whole lifetime and remaining lifetime, the data recorded in the recording unit of the laser apparatus produced by updating the data referenced in the middle of use can also be used as data for updating the data referenced upon calculation.

According to a twelfth aspect of the present invention, in the laser apparatus as described in any one of the first to eleventh aspects, the first calculation unit may calculate the acceleration factor as a product of a first acceleration factor depending on optical output from the light source or at least one drive condition value of the light source deciding the optical output, and a second acceleration factor depending on temperature detected by the temperature detection unit or a temperature of the light source obtained from the temperature detected by the temperature detection unit.

According to the laser apparatus as described in the twelfth aspect, in a case of the data to be referenced upon the first calculation unit calculating the acceleration factor being a two-dimensional data table that gives the acceleration factor relative to the two parameters of the drive condition value and temperature, the data volume required to be acquired from the past results data is large, and time is required in data acquisition; however, if expressing the acceleration factor by the product of the first acceleration factor depending on the drive condition value and the second acceleration depending on the temperature, it is possible to drastically reduce the data to be acquired, and thus possible to create the required data to be referenced in comparatively few man-hours.

According to a thirteenth aspect of the present invention, in the laser apparatus as described in the twelfth aspect, the first acceleration factor may be an acceleration factor at a condition fixing the temperature of the light source to the standard temperature, at which an acceleration effect on lifetime consumption caused by the temperature of the light source changing due to heat generation amount of the light source changing concomitant with the drive condition value changing is excluded; and the second acceleration factor may be an acceleration factor by the temperature of the light source.

According to the laser apparatus as described in the thirteenth aspect, for example, in the case of the drive condition value giving the acceleration factor being the driving current, since the first acceleration factor by the driving current will differ in accordance with the temperature, data for calculating each first acceleration factor relative to a plurality of temperatures is required for each; however, when detaching the influence on the acceleration of lifetime consumption due the change in temperature accompanying the change in drive condition, there is no need to provide data of acceleration factors by the driving current relative to a plurality of temperatures, and thus the required data volume further decreases, and the effect of the laser apparatus as described in the twelfth aspect in being able to create the data required to be referenced upon calculation with little workload becomes more remarkable.

According to a fourteenth aspect of the present invention, in the laser apparatus as described in the twelfth or thirteenth aspect, in a case of the light source being a laser diode or a laser diode module configured from a plurality of laser diodes, the temperature detection unit may be installed so as to detect temperature at any position on a thermal path from a pn junction of the laser diode until a cooling unit absorbing heat generated by the pn junction, and the first calculation unit may calculate the second acceleration factor relative to the temperature of the pn junction which is calculated from the temperature detected by the temperature detection unit, thermal resistance from a temperature detection position until the pn junction, and a heat generation amount of the pn junction calculated from an optical output characteristic of the light source.

According to the laser apparatus as described in the fourteenth aspect, in the case of the light source being a laser diode or a laser diode module configured from a plurality of laser diodes, if the temperature of the pn junction is known as the temperature of the light source, it is possible to use the Arrhenius model equation which is widely used in accelerated life testing, etc. in the calculation of the second acceleration factor. Although the temperature of the pn junction can be measured from a laser wavelength, etc., in many cases it is difficult to detect the temperature always, according to the above-mentioned method; however, it is possible to calculate the temperature of the pn junction according to the heat generation amount obtained from the optical output characteristic, and the thermal resistance from the temperature detection position until the pn junction, which can be estimated as constant.

According to a fifteenth aspect of the present invention, in the laser apparatus as described in any one of the twelfth to fourteenth aspects, in a case of the light source being a laser diode or a laser diode module configured from a plurality of laser diodes, the first calculation unit may calculate the first acceleration factor as an exponential function of an equation arrived at by dividing the drive condition value by a standard drive condition value, or an equation arrived at by dividing a value arrived at by subtracting a certain positive integer from the drive condition value, by a value arrived at by subtracting the certain positive integral from the standard drive condition value.

According to the laser apparatus as described in the fifteenth aspect, by way of configuring so as to also calculate the first acceleration factor with a mathematical formula, the data referenced upon calculation of the acceleration factor decreases, and the time required in data acquisition referenced upon calculation of the first acceleration factor is reduced. For the drive condition value for which the temperature of the pn junction changes as in optical output or driving current, by using a formula eliminating the influence of temperature accompanying the change in drive condition value, even if the temperature changes, the first acceleration factor can be calculated with the same formula; therefore, the reference data required upon calculation of the acceleration factor can be further decreased.

According to the laser apparatus according to the present invention, by calculating the effective driving time and effective cumulative driving time by time integrating an acceleration factor of the lifetime consumption taking into the consideration of the temperature of the light source in addition to the optical output or driving current, an effect is exerted in making so that evaluation of the length of the lifetime and the reliability of the light source as compared with the light source driven at the standard driving conditions can be carried out even in a case of the drive conditions including the temperature of the light source not being constant. In addition, it exerts an effect in making so that, if the effective cumulative driving time can be accurately calculated, it is possible to accurately estimate the remaining lifetime by comparison with data showing a relationship between a performance index derivable from an optical output characteristic corresponding to the effective cumulative driving time and the change rate of the performance index, and the remaining lifetime. The data showing the relationship between the performance index and the change rate of the performance index, and the remaining lifetime, corresponding to the effective cumulative driving time can be accumulated by leaving data of the performance index and the change rate of the performance index corresponding to the effective cumulative driving time as recordings, and can improve accuracy.

BRIEF DESCRIPTION OF THE DRAWINGS

FIG. 2 is a schematic view of an organizational example of data referenced upon a first calculation unit of the laser apparatus according to the first embodiment of the present invention calculating an acceleration factor;

FIG. 3 is a schematic view of an organizational example of data referenced upon a second calculation unit of the laser apparatus according to the first embodiment of the present invention calculating a whole lifetime;

FIG. 10 is a schematic view of an organizational example of data recorded in a recording unit of a laser apparatus according to a ninth embodiment of the present invention;

DETAILED DESCRIPTION OF THE INVENTION

Hereinafter, embodiments of the present invention will be explained based on the drawings.

First Embodiment

Figure 1:
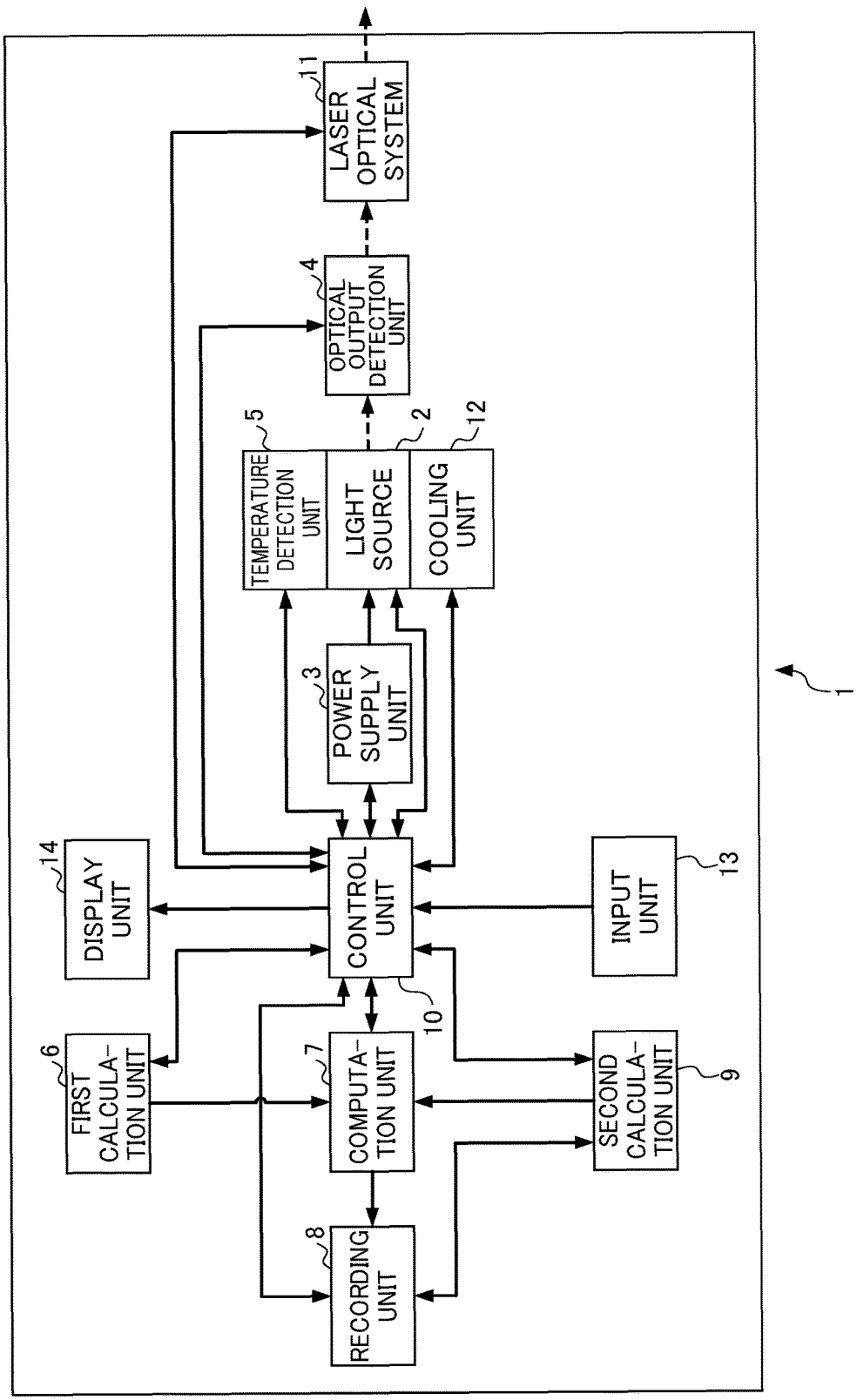
FIG. 1 is a schematic view showing the structure of a laser apparatus according to a first embodiment of the present invention.

FIG. 1 is a schematic view showing the structure inside a laser apparatus 1 according to a first embodiment of the present invention. As shown in FIG. 1, the laser apparatus 1 according to the first embodiment includes: at least one light source 2 that functions as a laser source or excitation light source; at least one power supply unit 3 that supplies driving current to the light source 2; at least one optical output detection unit 4 that detects the optical output from the light source 2; at least one temperature detection unit 5 that detects the temperature of the light source 2 or a member thermally connected to the light source 2; a first calculation unit 6 that calculates an acceleration factor F (P,T) of lifetime consumption of the light source 2, which depends on the temperature T and drive condition value P, based on a case of a temperature $T_M$ detected by the temperature detection unit 5 or a temperature $T_L$ of the light source 2 obtained from a temperature $T_M$ detected by the temperature detection unit 5 being a standard temperature $T_S$, and an optical output from the light source 2 or at least one drive condition value P of the light source 2 deciding the optical output being a standard condition value Ps; a second calculation unit 9 that calculates at least one lifetime among whole lifetime $\tau_L$ of the light source 2 and remaining lifetime $\tau_R$ of the light source 2 relative to at least one characteristic of the light source 2 among at least one performance index Q of the light source 2 which changes accompanying driving of the light source 2 and is obtainable from an optical output characteristic of the light source 2 and a change rate $\Delta Q/\Delta t$ of the performance index Q; a computational unit 7 that computes the time integral of the acceleration factor F (P,T) from a time $t_a$ until a time $t_b$ later than time $t_a$, i.e. Formula 1, as an effective driving time of the light source 2 from time $t_a$ until time $t_b$; a recording unit 8 that records the time integral of the acceleration factor F (P,T) computed by the computational unit 7 from a certain set time $t_s$ established until an arbitrary time $t_p$ later than the set time $t_s$, i.e. Formula 2, as an effective cumulative driving time $t_c$ until an arbitrary time $t_p$, and is capable of recording the whole lifetime $\tau_L$ and remaining lifetime $\tau_R$ calculated by the second calculation unit 9 with the optical output characteristic; and a control unit 10 that controls each of the units.

[Math. 1]

$$\int_{t_a}^{t_b} F(P(t), T(t)) \, dt \quad \text{(Formula 1)}$$

$$\int_{t_s}^{t_p} F(P(t), T(t)) \, dt \quad \text{(Formula 2)}$$

It should be noted that, in the present disclosure, the whole lifetime $\tau_L$ and remaining lifetime $\tau_R$ both indicate the whole lifetime or remaining lifetime when driving the light source 2 at the standard temperature Ts and standard drive condition value Ps. In addition, the temperature T is used as an abbreviation representing either temperature among the temperature $T_M$ detected by the temperature detection unit 5, or the temperature $T_L$ of the light source 2 obtained from the temperature $T_M$ detected by the temperature detection unit 5.

The optical output that was outputted from the light source 2 emits as a laser beam to outside of the laser apparatus 1 through a laser optical system 11 as illustrated in FIG. 1. In the case of the light source 2 being used as excitation light, a laser medium or the like such as Nd-doped YAG crystal or Yb-doped fiber laser which converts the excitation light into a laser beam is necessary; however, the laser optical system 11 indicates an optical system including a laser medium, optical coupling, focused-imaging formation optical system, optical coupling optical system, optical branching optical system, machining head with built-in optical system, etc., as necessary. In addition, the beam is schematically represented by the dotted arrow; however, it is not limited to a beam propagated in space, and may be light that propagates within fiber. The installation location of the optical output detection part 4 configured by photodiodes, etc. is not limited to the position shown in FIG. 1, and may detect a laser beam after propagating in the laser optical system 11. In addition, the detection method of optical output is not limited to that arrangement shown in FIG. 1, and in the case of a laser beam propagating in space, a part of the laser beam may be made incident on the optical output detection part 4 by a half mirror, and in the case of the laser beam propagating within fiber, leaked light from the cladding may be detected, and the optical output detection part 4 may be installed at an end of branching fiber.

It should be noted that, in order to suppress a temperature rise of the light source 2 due to heat generation of the light source 2, it is desirable for the light source 2 to thermally connect with a cooling unit 12. The cooling unit 12 is a water-cooling plate in the case of water cooling, a heat sink equipped with radiating fins in the case of air cooling, or the like.

In addition, the laser apparatus 1 may include an input unit 13 for inputting commands from outside of the control unit 10, or a display unit 14 that displays computation results from the computation unit 7, etc.

FIG. 2 is a graph for explaining examples of a method for calculating the acceleration factor F (P,T) for lifetime consumption of the light source 2 relative to the temperature T detected by the temperature detection unit 5 and the drive condition value P of the light source 2, which defines a case of the temperature T being the standard temperature Ts, and the drive condition value P is the standard drive condition value Ps as the reference F (Ps,Ts) being 1, in which the first calculation unit 6 can include two-dimensional data tables from which the acceleration factor F (P,T) can be read when designating the temperature T and drive condition value P, such as shown in FIG. 2. As shown in FIG. 2, the lifetime becomes shorter with larger drive condition value P such as the optical output or driving current. In other words, in the case of the acceleration factor F (P,T) of the lifetime consumption being large, the acceleration factor F (P,T) becomes a larger acceleration factor with larger P and with higher T, and in the case of T<Ts and P<Ps, F (P,T) will be less than 1. It should be noted that the data table such as that of FIG. 2 can be created based on past results data. It should be noted that, in the case of data for which the drive condition value P and temperature T match not being in the data table, it is sufficient to calculate the acceleration factor by interpolation or the like.

When time integrating this acceleration factor F (P,T) from time $t_a$ until time $t_b$ which is later than time $t_a$, the effective driving time from $t_a$ to $t_b$ of the light source 2 can be computed. For example, in the case of the acceleration factor F (P,T) being 2, the effective driving time is calculated as twice the actual driving time. It should be noted that, since the acceleration factor is 0 at times not driving the light source 2, it is not factored into the effective driving time even when time integrating.

If setting the start time $t_s$ for time integration to after shipping data acquisition completion of the light source or after burn-in completion, for example, the effective cumulative driving time $t_c$ from the setting time $t_s$ until time $t_p$ taking into consideration both drive conditions such as the temperature of the light source 2 and the optical output or driving current, can be computed by time integration of the acceleration factor F (P,T) from time $t_s$ until time $t_p$.

Even if the temperature of the light source 2 changes, since the effective cumulative driving time $t_c$ arrived at by converting to the case of driving at the standard temperature Ts and standard drive condition value Ps can be calculated even when changing the drive conditions, lifetime management is possible, and it becomes possible to quantitatively evaluate the lifetime and reliability.

The effective cumulative driving time $t_c$ calculated by the computation unit 7 may be recorded in a state continually updated in the recording unit 8 by adding the time integrated value while the light source 2 is being driven. In order to leave the driving history, it is desirable to be able to record in the recording unit 8, not only the latest effective cumulative driving time $t_c$, but also the measured optical output characteristic of the light source 2, whole lifetime $\tau_L$ or remaining lifetime $\tau_R$ estimated for the light source 2.

FIG. 3 is a graph for explaining an example of a method for calculating, in the second calculation unit 9, at least one lifetime among the whole lifetime $\tau_L$ or remaining lifetime $\tau_R$ of the light source 2 relative to at least one characteristic of the light source 2 among at least one performance index Q that can be obtained from the optical output characteristic of the light source 2 which changes accompanying driving of the light source, and a change rate $\Delta Q/\Delta t$ of the performance index Q, in which the second calculation unit 9 can include data from the which the whole lifetime $\tau_L$ of the light source 2 estimated from the performance index Q at the setting time $t_s$, for example, as shown in FIG. 3, can be read. Data in the form of a graph showing the relationship between the performance index Q and whole lifetime $\tau_L$ of the light source 2 may be included. The performance index Q is data such as that shown in FIG. 3 in the case of estimating as having better performance and longer whole lifetime $\tau_L$ with a larger performance index Q as in the optical output obtained at a predetermined driving current, for example. Conversely, the performance index Q shows the opposite relationship to FIG. 3, in the case of estimating longer whole lifetime $\tau_L$ with a lower performance index Q as in the driving current required to obtain a predetermined optical output. Data such as that in FIG. 3 can be created based on past results data.

According to the above explained first embodiment, even if the drive conditions such as the temperature of the light source 2 and the optical output or driving current change, since the effective driving time converted to the driving time for the case of driving the light source 2 at the standard temperature Ts and the standard drive condition value Ps, and effective cumulative driving time $t_c$ can be calculated, it comes to be possible to quantitatively evaluate the lifetime or reliability of the light source 2. In addition, since it is possible to estimate with high accuracy the whole lifetime $\tau_L$ or remaining lifetime $\tau_R$ of the light source 2 due to calculating the whole lifetime $\tau_L$ or remaining lifetime $\tau_R$ of the light source 2 by considering the characteristic individual variation in the performance index Q of the light source 2 or change rate of the performance index Q, it is possible to perform scheduled replacement, etc. of the light source 2 without leading to a situation such as the lifetime of the light source 2 being exhausted unexpectedly, and the laser apparatus 1 not being able to be used for a long time, and thus the productivity of the laser apparatus 1 improves. Furthermore, since it is possible to record the calculated whole lifetime $\tau_L$ or remaining lifetime $\tau_R$, and optical output characteristic of the light source, along with recording the effective cumulative driving time $t_c$, in a case of leaving the whole lifetime $\tau_L$ or remaining lifetime $\tau_R$, or optical output characteristic in the recording, it is possible to verify the calculation accuracy of the first calculation unit 6 or second calculation unit 9, and thus it is possible to use as information for further improving the calculation accuracy.

Second Embodiment

Figure 4:
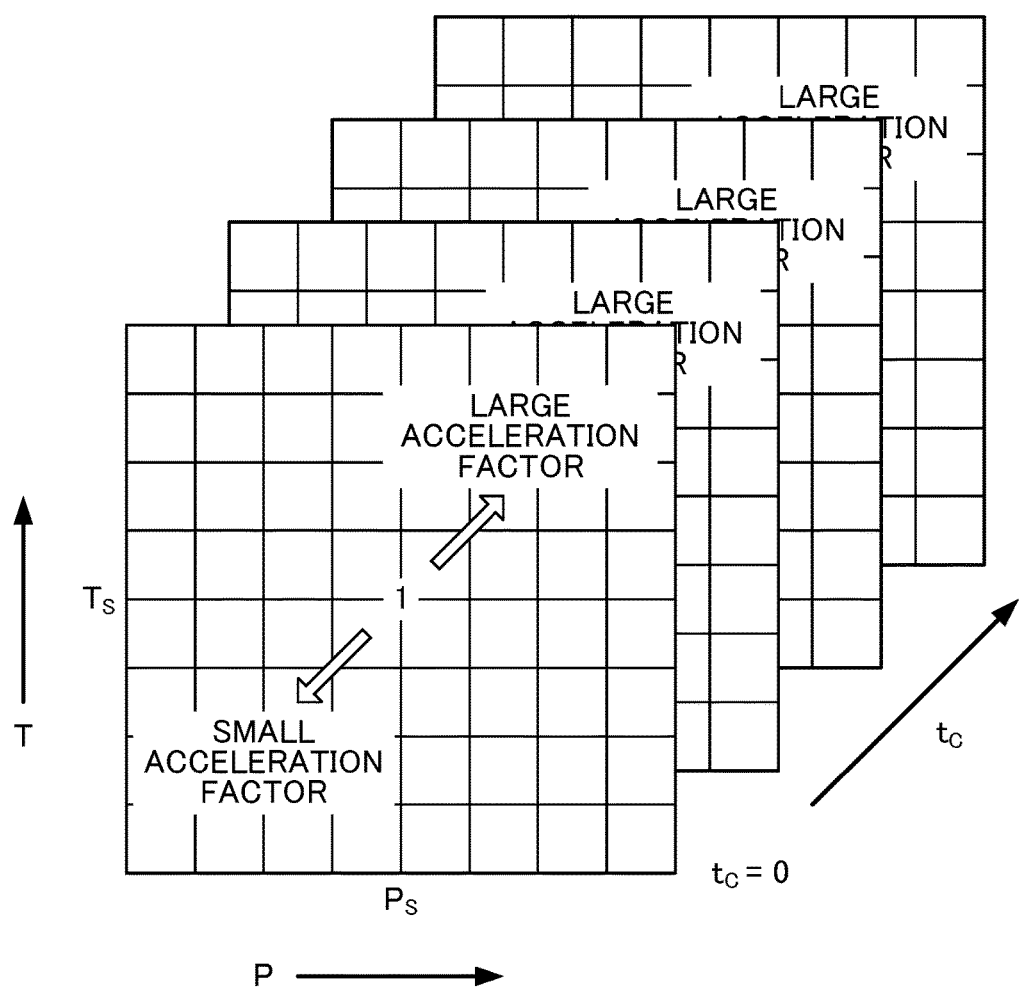
FIG. 4 is a schematic view of an organizational example of data referenced upon a first calculation unit of the laser apparatus according to a second embodiment of the present invention calculating an acceleration factor.

In a laser apparatus according to a second embodiment of the present invention, the dependence on the effective cumulative driving time $t_c$ is also considered in the acceleration factor F (P,T) calculated by the first calculation unit 6. FIG. 4 shows an organizational example of a data table referenced by the laser apparatus of a second example upon calculation of the acceleration factor F (P,T). A two-dimensional data table of one layer shown in FIG. 2 is included for each of a plurality of effective cumulative driving times. Upon referencing the data table of FIG. 4, in the case of there not being a data table in which effective cumulative driving time $t_c$ matches, it is possible to calculate the acceleration factor F (P,T) by interpolation, etc. When reaching the lifetime late stage, for the acceleration factor F (P,T) larger than the reference value being 1, even if the drive condition value P and temperature T are the same, there is a tendency for the acceleration factor F (P,T) to gradually increase; however, even in the case of the acceleration factor F (P,T) differing according to the effective cumulative driving time $t_c$, an accurate effective driving time or effective cumulative driving time $t_c$ can be calculated. For the lifetime early stage, since the change in acceleration factor F (P,T) is small, the interval of the effective cumulative driving time $t_c$ between two-dimensional data tables of FIG. 4 may be large.

Third Embodiment

In a laser apparatus according to a third embodiment of the present invention, the second calculation unit 9 can calculate the remaining lifetime $\tau_R$ of the light source 2 at an arbitrary time $t_p$ by subtracting the effective cumulative driving time $t_c$ until the arbitrary time $t_p$ recorded in the recording unit 8, from the whole lifetime $\tau_L$ of the light source 2 calculated relative to at least one characteristic of the light source 2 among the performance index Q of the light source 2 and the change rate of the performance index Q. In other words, it is possible to calculate as $\tau_R = \tau_L - \tau_c$. The second calculation unit 9 can calculate the remaining lifetime $\tau_R$ by subtracting the effective cumulative driving time $t_c$ from the whole lifetime $\tau_L$ of the light source 2 calculated from the initial characteristic of the performance index Q, e.g., performance index Q at the setting time $t_s$ (i.e. effective cumulative driving time $t_c=0$). Since the individual variations in light sources 2 such as the initial characteristic of the performance index Q is being take into consideration, an accurate remaining lifetime $\tau_R$ can be calculated. In addition, an accurate remaining lifetime can be calculated from the lifetime initial stage prior to characteristic degradation of the light source 2 manifesting. For this reason, since the replacement period of the light source 2 can be known from early, for example, it becomes possible to systematically budget the replacement costs of the light source 2.

Fourth Embodiment

In a laser apparatus according to a fourth embodiment of the present invention, according to a command from the control unit 10, it is possible for the power supply unit 3 to output the driving current for optical output measurement to the light source 2 following a predetermined schedule, for the control unit 10 to measure the optical output characteristic of the light source 2 representing a relationship between the driving current and the optical output detected by the optical output detection unit 4, and for the recording unit 8 to add or record the optical output characteristic in the recording unit 8 to be associated with the effective cumulative driving time $t_c$ at this moment.

Figure 5:
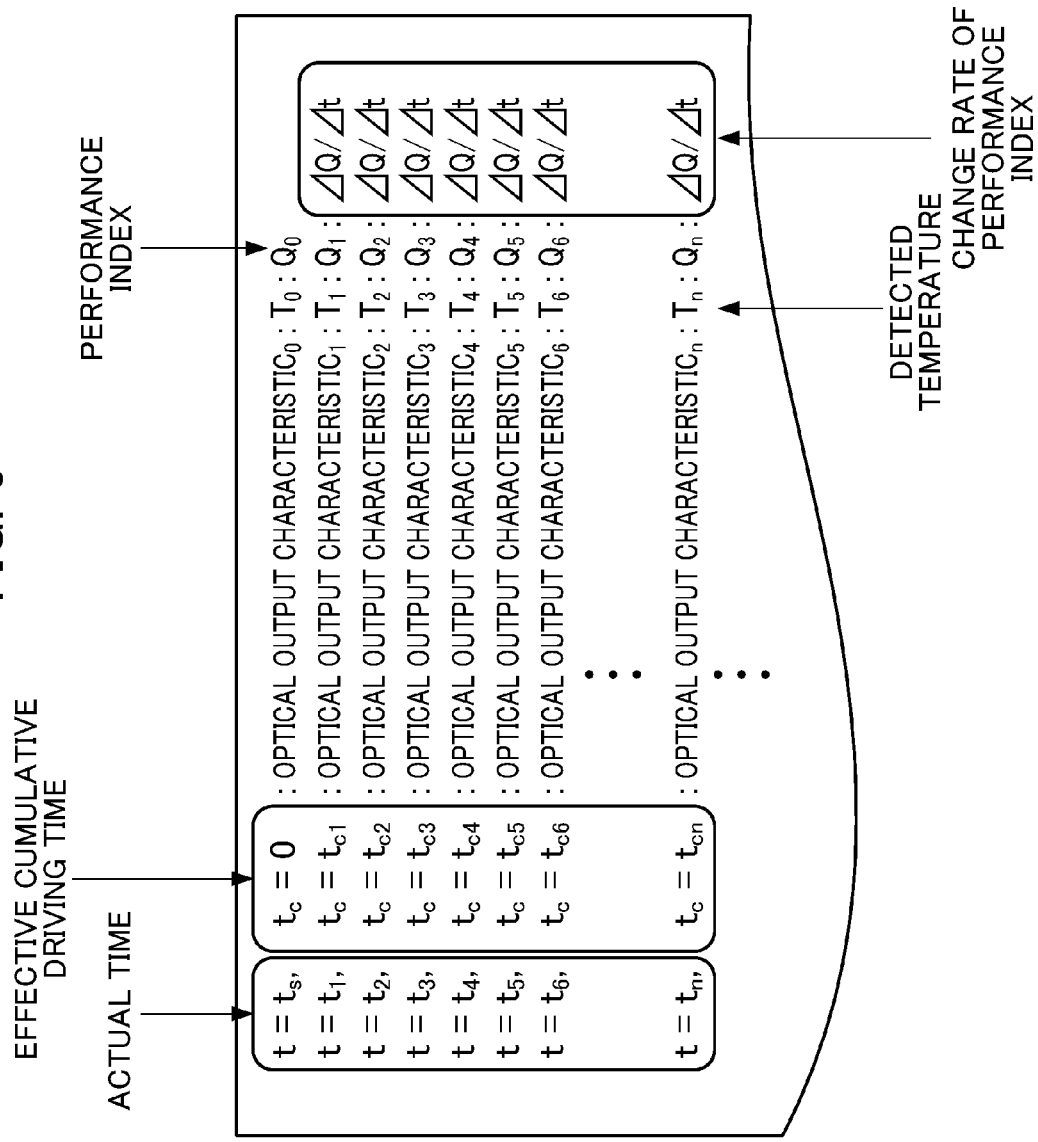
FIG. 5 is a schematic view of an organizational example of data recorded in a recording unit of a laser apparatus according to a fourth embodiment of the present invention.

FIG. 5 schematically shows an organizational example of data recorded in the recording unit 8, which can be made by, after recording the optical output characteristic of the light source 2 at the setting time $t_s$ (i.e. effective cumulative driving time $t_c=0$), which is the count start moment of the effective cumulative driving time $t_c$, and the detected temperature T when measuring the optical output characteristic, for example, adding the effective cumulative driving time $t_c$, optical output characteristic and detected temperature T when measuring the optical output characteristic, every time measuring the optical output characteristic of the light source 2 following a predetermined schedule. It should be noted that the triangular symbols at the upper right in the drawing indicate the same as "$\Delta$". Since it is believed to be useful in investigation, etc. in the case of abnormal data being recorded, the real time (actual time) t may be written together with the effective cumulative driving time $t_c$, as shown in FIG. 5. In addition, since the performance index Q obtainable from the optical output characteristic of the light source 2 is, for example, the optical output obtained at a predetermined driving current or the driving current required for obtaining a predetermined optical output, etc., and can be calculated even later on so long as the optical output characteristic is recorded, the matter of leaving a recording in the recording unit 8 is not an essential requirement; however, the performance index Q and the change rate $\Delta Q/\Delta t$ of the performance index Q referenced upon calculation of the remaining lifetime $\tau_R$ of the light source 2 may be jointly written. The change rate $\tau Q/\tau t$ of the performance index is a value arrived at by dividing the difference $\tau Q$ in the performance index Q by the difference $\Delta t$ in the effective cumulative driving time $t_c$ during the time, and the change rate of the performance index $(\Delta Q/\Delta t) t_c = t_{cn}$ for the effective cumulative driving time $t_c = t_{cn}$ is a value that can be calculated by $(Q_n - Q_{(n-1)})/(t_{cn} - t_{c(n-1)})$, and can be calculated accurately only when an accurate effective cumulative driving time $t_c$ can be calculated.

By leaving the measured optical output characteristic of the light source 2 in the recording to be associated with the effective cumulative driving time $t_c$, for the performance index Q that can be obtained from the optical output characteristic as mentioned above, it is possible to know the variation range $\Delta Q$, and since the change rate $\Delta Q/66$ t of the performance index Q is obtained by dividing the variation range $\Delta Q$ by the difference in effective cumulative driving time $\Delta t$, a remaining lifetime $\tau_R$ that takes into account the individual variation including the degradation rate in characteristic of the light source 2 comes to be calculatable. In addition, by performing by adding the optical output characteristic, it is possible to leave a history of the optical output characteristic and change in performance index accompanying the elapse of effective cumulative driving time $t_c$, and thus it is possible to use as information for further improving the calculation accuracy of the first calculation unit 6 and second calculation unit 9. By updating the optical output characteristic of the light source 2 obtained from the optical output detected by changing the driving current, there is an effect of accurate optical output relative to the optical output command becoming possible.

Figure 6:
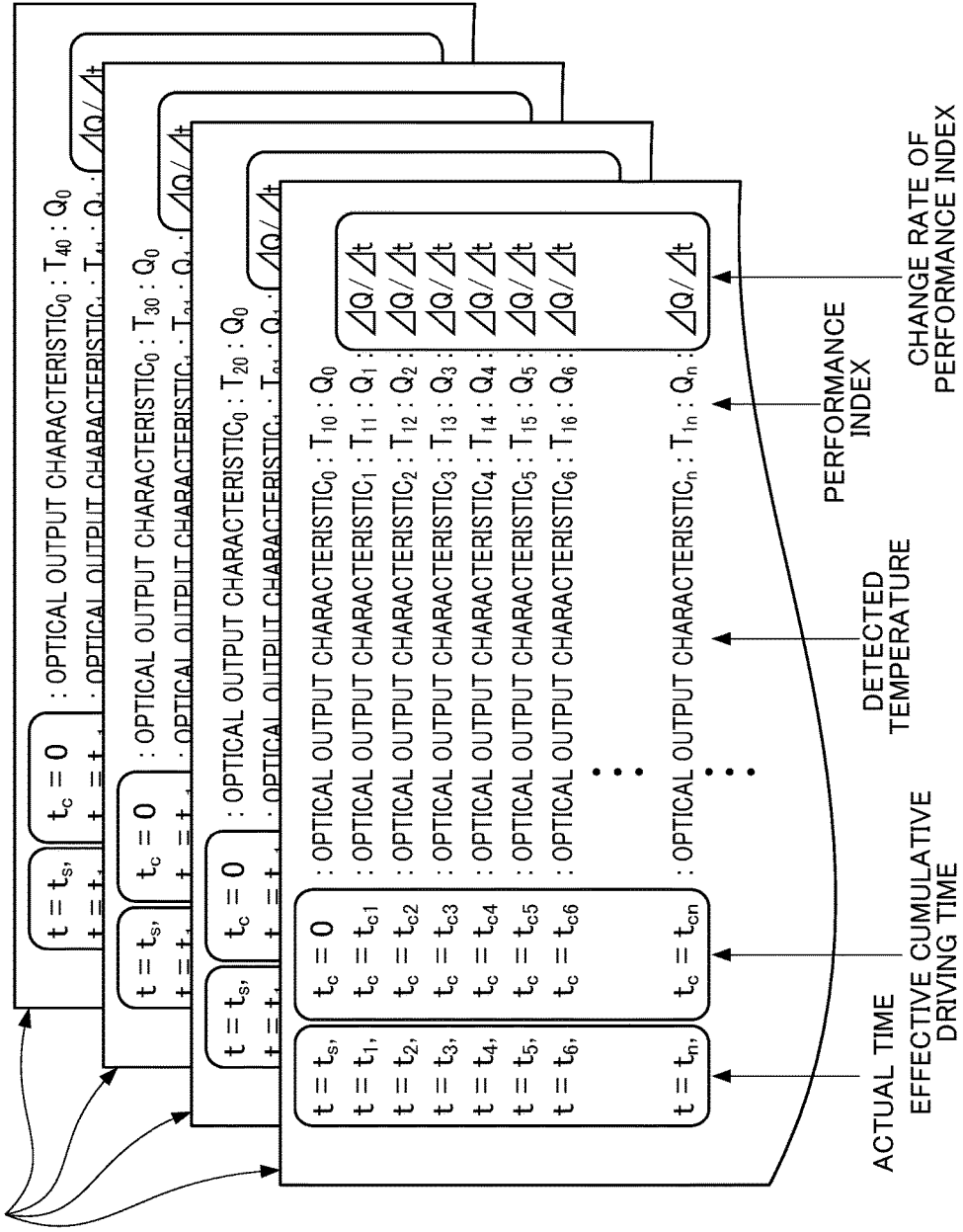
FIG. 6 is a schematic view of another organizational example of data recorded in a recording unit of a laser apparatus according to the fourth embodiment of the present invention.

It should be noted that, although there is a general rule of measuring the optical output characteristic at time when the detected temperature T is substantially the same temperature, if adopting a plurality of temperatures as measurement conditions of the optical output characteristic, it is possible to avoid missing the data update timing of the optical output characteristic by waiting for the time when the temperature becomes the same as the temperature set in the measurement conditions. In this case, it is sufficient to record data at every different detected temperature in the recording unit 8, as shown in FIG. 6. The detection temperature may be adjusted to a measurement planned temperature for optical output by secondarily controlling the fan air flow, heater heating value, cooling capability of the electric cooling element, etc.

Fifth Embodiment

Figure 7:
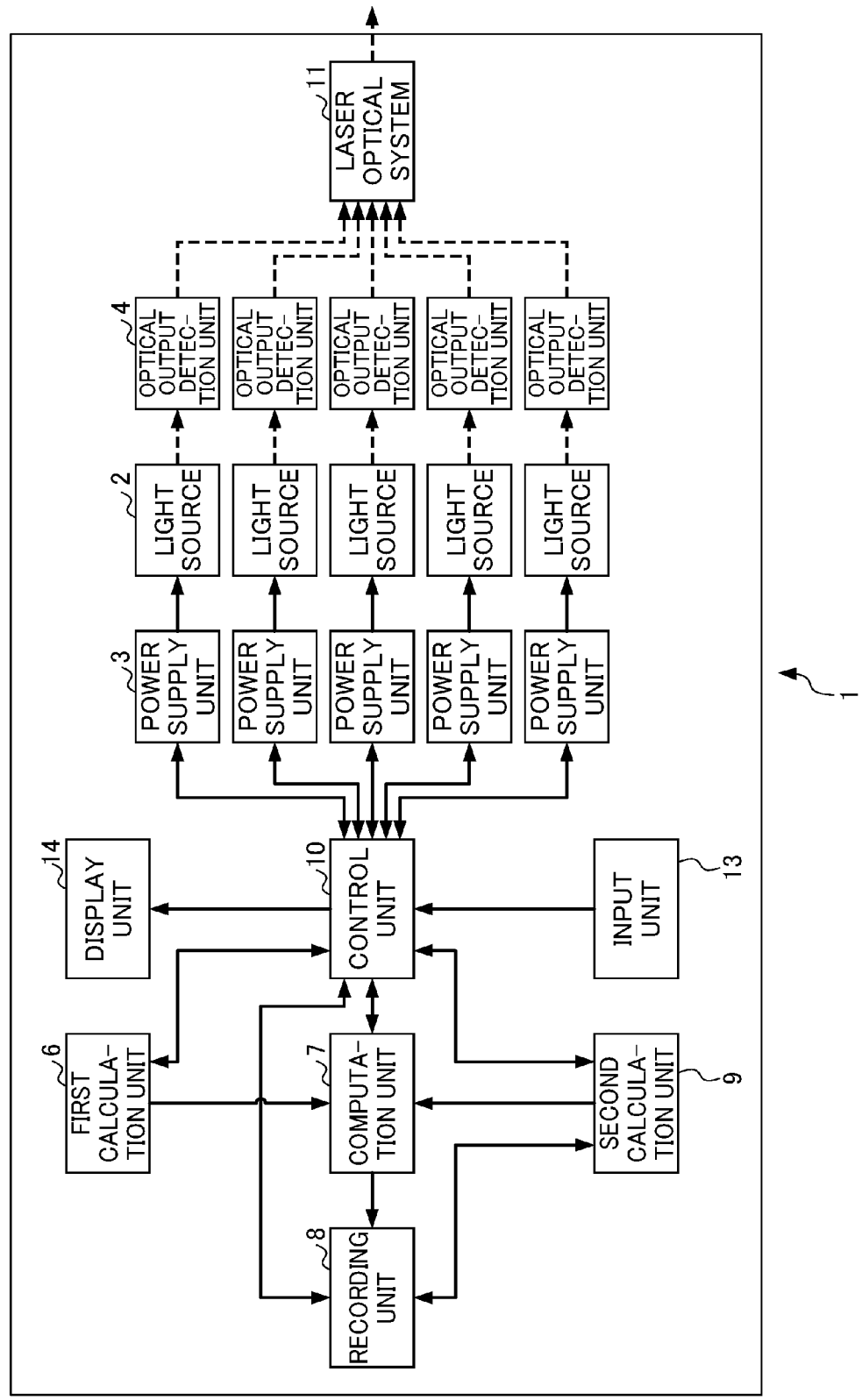
FIG. 7 is a schematic view showing the structure of a laser apparatus according to a fifth embodiment of the present invention.

FIG. 7 is a schematic view showing the structure within a laser apparatus according to a fifth embodiment of the present invention. As shown in FIG. 7, a plurality of light sources 2 which can independently control the driving current are included, and it is possible to include at least one optical output detection part 4 capable of detected the optical output relative to each of the light sources 2 capable of independently controlling the driving current. Since it is possible to simultaneously measure the optical output characteristic of a plurality of light sources 2, the optical output characteristic can be measured in a short time, and an accurate input/output characteristic can be measured even with an air-cooled laser apparatus having unstable temperature. It should be noted that, since the drawing would become complicated, the temperature detection unit 5 and cooling unit 12 thermally connected to the light source 2 are omitted from FIG. 7. In addition, the signal lines connecting the light source 2, temperature detection unit 5, laser optical system 11 and control unit 10 are also omitted. Furthermore, the laser optical system 11 is described as including an optical coupler.

In addition, in the case of a plurality of the light sources 2 drivable at independent drive conditions being present, for the data recorded in the recording unit 8, it is sufficient to leave data of an organization as shown in FIG. 5 or 6 for every light source in the recording.

It should be noted that, in the case of including a plurality of light sources 2 capable of independently controlling the driving current, by referencing the remaining lifetime $\tau_R$ of each light source 2, it becomes possible to preferentially drive the light source 2 having the relatively longer remaining lifetime $\tau_R$, or increase the allotted amount of driving current to light source 2 having the relatively longer remaining lifetime $\tau_R$, thereby align the time periods at which the lifetime of each light source will be exhausted, and lengthen the lifetime as an overall laser apparatus.

Sixth Embodiment

Figure 8:
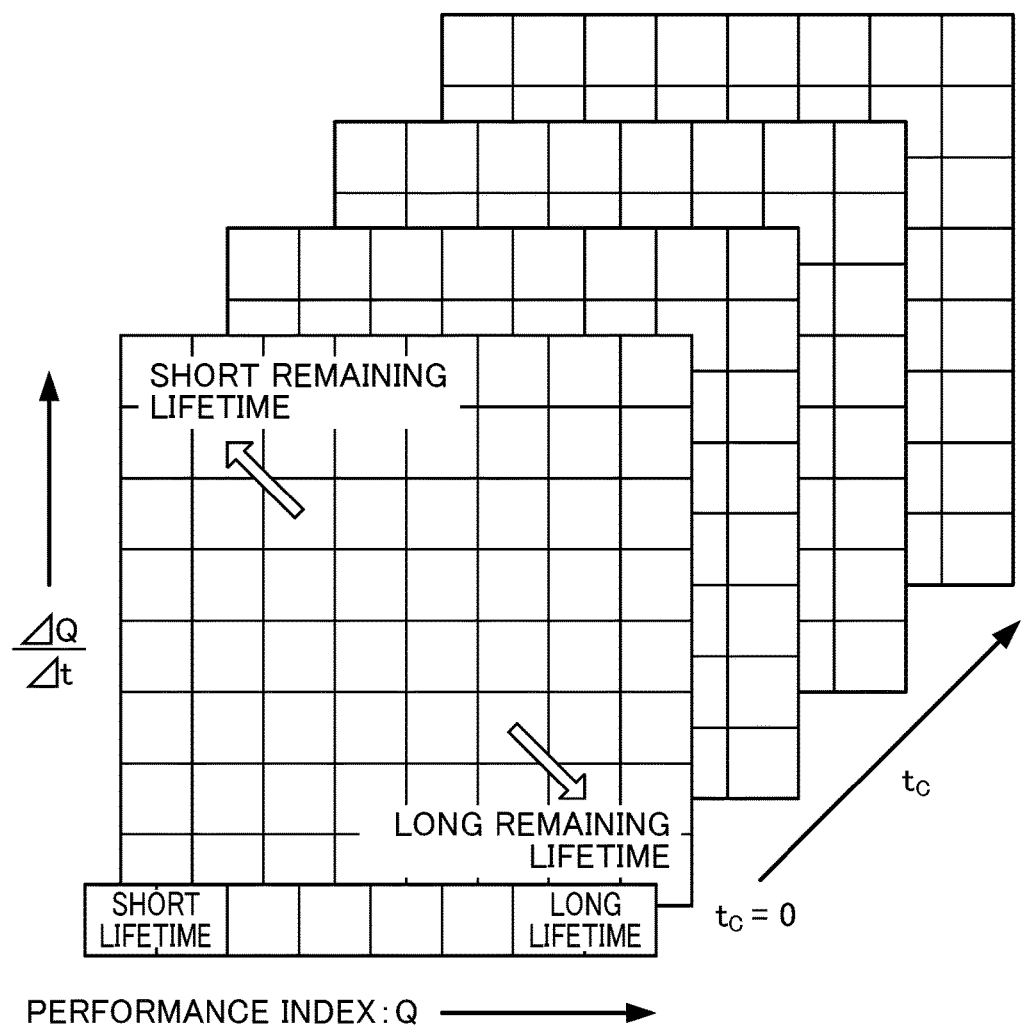
FIG. 8 is a schematic view of an organizational example of data referenced upon a second calculation unit in a laser apparatus according to a sixth embodiment of the present invention calculating a remaining lifetime or whole lifetime.

In a laser apparatus according to a sixth embodiment of the present invention, the dependence of the remaining lifetime $\tau_R$ calculated by the second calculation unit 9 on the effective cumulative driving time $\tau_c$ is taken into consideration in the performance index Q of the light source 2 and the change rate of the performance index Q. FIG. 8 schematically shows an organizational example of a data table referenced by the laser apparatus of the sixth embodiment upon calculation of the remaining lifetime $\tau_R$. The data table of FIG. 8 is a data table of the remaining lifetime $\tau_R$ in the case of the characteristic of the light source 2 being better and the remaining lifetime $\tau_R$ being longer with greater performance index Q that can be obtained from the optical output characteristic of the light source 2, such as the optical output obtained at a predetermined driving current, and two-dimensional data tables of longer remaining lifetime $\tau_R$ with higher performance index Q and smaller change rate of the performance index Q are included relative to a plurality of effective cumulative driving times $t_c$. The remaining lifetime $\tau_R$ can be calculated by reading out the remaining lifetime $\tau_R$ from a point at which the performance index Q and the change rate $\Delta Q/\Delta t$ of the performance index Q match on the two-dimensional data table with which the effective cumulative driving time $t_c$ matches. In a case of there not being data at the point at which the performance index Q and the change rate $\Delta Q/\Delta t$ of the performance index Q match, the remaining lifetime $\tau_R$ can be calculated by interpolation. In addition, in the case of there being no data table with which the effective cumulative driving time $t_c$ matches, the remaining lifetime $\tau_R$ can be calculated by interpolation or the like. The two-dimensional data table for reading the remaining lifetime $\tau_R$ from the point at which the performance index Q and the change rate $\Delta Q/\Delta t$ of the performance index Q match is recorded relative to a discrete effective cumulative driving time $t_c$; however, it is desirable to widen the time interval for the lifetime initial stage until the performance index Q starts to change, and shorten the time interval for the lifetime late stage at which the change in performance index Q starts to manifest. A predetermined schedule may be set so that the measurement timing of the optical output characteristic matches with the effective cumulative driving time $t_c$ of the plurality of two-dimensional data tables referenced by the first calculation unit 6 or second calculation unit 9. It should be noted that the data when the effective cumulative driving time $t_c$=0 in FIG. 8 is the same data as the data illustrated in FIG. 3.

According to the present embodiment, for example, even with the same change rate $\Delta Q/\Delta t$ of the performance index Q and the same performance index Q, for a light source 2 having a short effective cumulative driving time $t_c$, it means that degradation started from early on, and there are more degradation factors than usual; therefore, although from thereon the degradation advances rapidly and the remaining lifetime $\tau_R$ is estimated as short, calculation by the second calculation unit 9 of a higher accuracy remaining lifetime $\tau_R$ in which the individual variation in degradation states of the light sources 2 is accurately reflected becomes possible by taking account of the effective cumulative driving time $t_c$ of the light source 2, in addition to the performance index Q of the light source 2 and the change rate $\Delta Q/\Delta t$ of the performance index Q. In other words, since the remaining lifetime $\tau_R$ for the lifetime late stage at which the characteristic degradation of the light source 2 is manifesting is calculated by taking consideration of individual variations in characteristic and change rate thereof, the remaining lifetime $\tau_R$ can be calculated with good accuracy even at the lifetime late stage. It should be noted that the change rate of the performance index Q required in estimation of the remaining lifetime $\tau_R$ with good accuracy can be accurately calculated only when there is an effective cumulative driving time $t_c$ calculated with good accuracy.

Seventh Embodiment

In a laser apparatus according to a seventh embodiment of the present invention, in a case of the change rate $\Delta Q/\Delta t$ of the performance index Q or variation range $\Delta Q$ obtained from the optical output characteristic recorded or added to the recording unit 8 to be associated with the effective cumulative driving time $t_c$ exceeding a predetermined value which exceeds a measurement error for the optical output characteristic, it includes a function of replacing the whole lifetime $\tau_L$ calculated by the second calculation unit 9 based on a past performance index Q of the light source 2 or change rate $\Delta Q/\Delta t$ of the performance index Q, with a value arrived at by adding the effective cumulative driving time $t_c$ to the remaining lifetime $\tau_R$ of the light source 2 calculated from the performance index Q of the light source 2 obtained from the newly measured optical output characteristic of the light source 2 and the change rate $\Delta Q/\Delta t$ of the performance index Q, i.e. $\Delta_R + t_c$.

When characteristic degradation of the light source 2, i.e. change in performance index Q, manifests, since the remaining lifetime $\tau_R$ directly calculated by the method of the sixth embodiment from the most recent performance index Q of the light source 2 and change rate $\Delta Q/\Delta t$ of the performance index Q is higher accuracy than the remaining lifetime $\tau_R$ obtained by subtracting the effective cumulative driving time $t_c$ from the whole lifetime $\tau_L$ calculated in the past, it is possible to update to an accurate whole lifetime $\tau_L$. In addition, a high accuracy remaining lifetime $\tau_R$ can be calculated without changing the function of the third embodiment at the lifetime late stage, by way of updating of the whole lifetime $\tau_L$.

Eighth Embodiment

Figure 9:
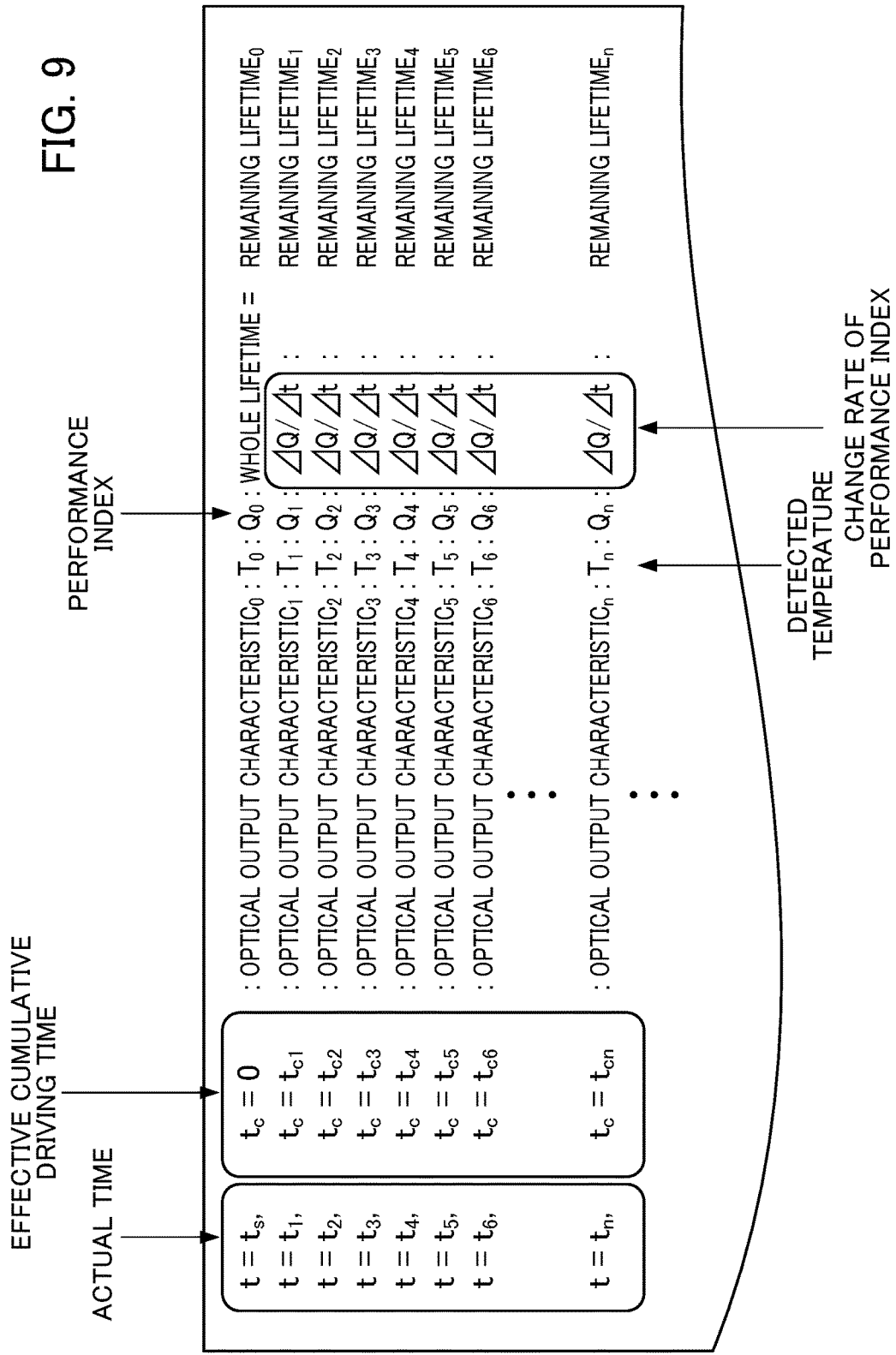
FIG. 9 is a schematic view of an organization example of data recorded in a recording unit of a laser apparatus according to an eighth embodiment of the present invention.

In a laser apparatus according to an eighth embodiment of the present invention, the recording unit 8 can include a function of recording or adding the remaining lifetime $\tau_R$ of the light source 2 at the effective cumulative driving time $t_c$ calculated by the second calculation unit 9, together with the optical output characteristic recorded or added to be associated with the effective cumulative driving time $t_c$ in the recording unit 8. FIG. 9 is a schematic view showing an organizational example of data recorded in the recording unit 8, and the accuracy of the whole lifetime $\tau_L$ or remaining lifetime $\tau_R$ calculated from the performance index Q calculated from the optical output or the change rate $\Delta Q/\Delta t$ of the performance index Q can be verified at the stage at which the lifetime is exhausted, by leaving history of the optical output relative to the elapse of effective cumulative driving time $t_c$ and the remaining lifetime $\tau_R$ calculated by the second calculation unit 9, and further, it is possible to use as information for improving the calculation accuracy of the first calculation unit 6 or second calculation unit 9. For example, it becomes possible to calculate the average value for the effective cumulative driving time $t_c$ by collecting data for which the performance index Q and change rate $\Delta Q/\Delta t$ of the performance index Q are the same, and in the case of this average value deviating from the remaining lifetime $\tau_R$ listed in the two-dimensional data table referenced by the second calculation unit 9, update the two-dimensional data table referenced by the second calculation unit 9 so that the deviation decreases, etc.

Ninth Embodiment

In a laser apparatus according to a ninth embodiment of the present invention, the recording unit 8 can have a function of recording or adding the temperature T detected by the temperature detection unit 5 or the temperature of the light source 2 obtained from the temperature detected by the temperature detection unit 5, and the drive condition value P of the light source 2, in a period from a measurement time of the optical output characteristic until a subsequent measurement time of the optical output characteristic, along with the optical output characteristic recorded or added to be associated with the effective cumulative driving time $t_c$ in the recording unit 8.

FIG. 10 is a schematic view showing an organizational example of data recorded in the recording unit 8, and when recording information related to drive conditions including the temperature of the light source 2 from a measurement time of the optical output characteristic until a subsequent measurement of the optical output characteristic, it is possible to verify that the acceleration factor F (P,T) relative to the drive condition during this time is not an overestimation or underestimation, and it is possible to use as information for improving the calculation accuracy of the first calculation unit 6. For example, at a certain effective cumulative driving time $t_c$, in the case of collecting data for which the performance index Q and the change rate $\Delta Q/\Delta t$ of the performance index Q are the same and viewing the distribution of the remaining lifetime $\tau_R$, and the data of drive conditions with high temperature T being unevenly distributed at longer remaining lifetime $\tau_R$, it is possible to show the matter of overestimating the acceleration factor F (P,T)

due to the rise in temperature T, and the effective driving time being calculated to be longer, then revise and update the two-dimensional data table referenced by the first calculation unit 6 so as to eliminate the above-mentioned uneven distribution, and thus improve the calculation accuracy of the first calculation unit 6. If the calculation accuracy of the first calculation unit 6 improves, since the calculation accuracy of the effective driving time improves, the update accuracy of the data table referenced by the second calculation unit will rise in a ripple manner, and it is also possible to improve the calculation accuracy of the second calculation unit 9. In order to acquire data easily used in the update of the data table, drive conditions such as the detected temperature T and drive condition value P may be recorded in the recording unit 8 along with the effective cumulative driving time $t_c$, optical output characteristic, performance index Q, change rate $\Delta Q/\Delta t$ of the performance index Q, remaining lifetime $\tau_R$, etc. by measuring the optical output characteristic every time the drive conditions including temperature change.

Tenth Embodiment

In a laser apparatus according to a tenth embodiment of the present invention, it is possible to output data such as that of FIGS. 5, 6, 9 and 10 recorded in the recording unit 8, to a computing system, server or the like for which the accumulation or analysis of data is possible by way of a recording medium or communication means. As mentioned above, by collecting and analyzing the data recorded in the recording unit 8, also including the effective cumulative driving time $t_c$ at the moment at which the lifetime of the light source 2 actually is exhausted, it is possible to compare the whole lifetime $\tau_L$ or remaining lifetime $\tau_R$ calculated by the first calculation unit 6 or second calculation unit 9 with the actual whole lifetime or remaining lifetime, and thus it is possible to revise and update the data table referenced by the first calculation unit 6 or second calculation unit 9 upon calculation so that the difference therebetween decreases. As a result thereof, it is possible to further improve the calculation accuracy of the effective cumulative driving time $t_c$, whole lifetime $\tau_L$ and remaining lifetime $\tau_R$.

A network and server may be used for collecting the extensive data from many laser apparatuses, and artificial intelligence or a machine learning device may be used in order to analyze the vast data and update the database referenced by the first calculation unit 6 or second calculation unit 9 upon calculating the acceleration factor F (P,T) or remaining lifetime $\tau_R$. There is no necessity for the database referenced by the first calculation unit 6 or second calculation unit 9 upon calculating the acceleration factor F (P,T) or remaining lifetime $\tau_R$ to exist inside of the laser apparatus 1, and in order to achieve together with a real-time property, for example, may include a server of a fog computing system or the like, and calculate the acceleration factor F (P,T) or remaining lifetime $\tau_R$ by referencing the database through a network. In addition, it may be configured so as to also record the data recorded in the recording unit 8 in a server or the like connected by a network.

In addition, it may be configured so that a reminder to the client or preparation of a light source 2 to be replaced is performed so as to curb the time for which the laser apparatus 1 cannot operate to a minimum, by configuring so as to automatically output in a timely manner information such as the remaining lifetime $\tau_R$ to the manufacturer or maintenance contracted vendor of the laser apparatus 1 through a network or the like.

Eleventh Embodiment

In a laser apparatus according to an eleventh embodiment of the present invention, at least one set of data among data referenced by the first calculation unit 6 upon calculation of the acceleration factor F (P,T) and data referenced by the second calculation unit 9 upon calculating the whole lifetime $\tau_L$ or remaining lifetime $\tau_R$ of the light source 2 can be substituted by data by way of a recording medium or communication means, even at a moment at which the effective cumulative driving time $t_c$ of the laser apparatus 1 elapsed, and it is possible to leave a recording of at which moment of effective cumulative driving time $t_c$ the data was substituted in the recording unit 8.

Figure 11:
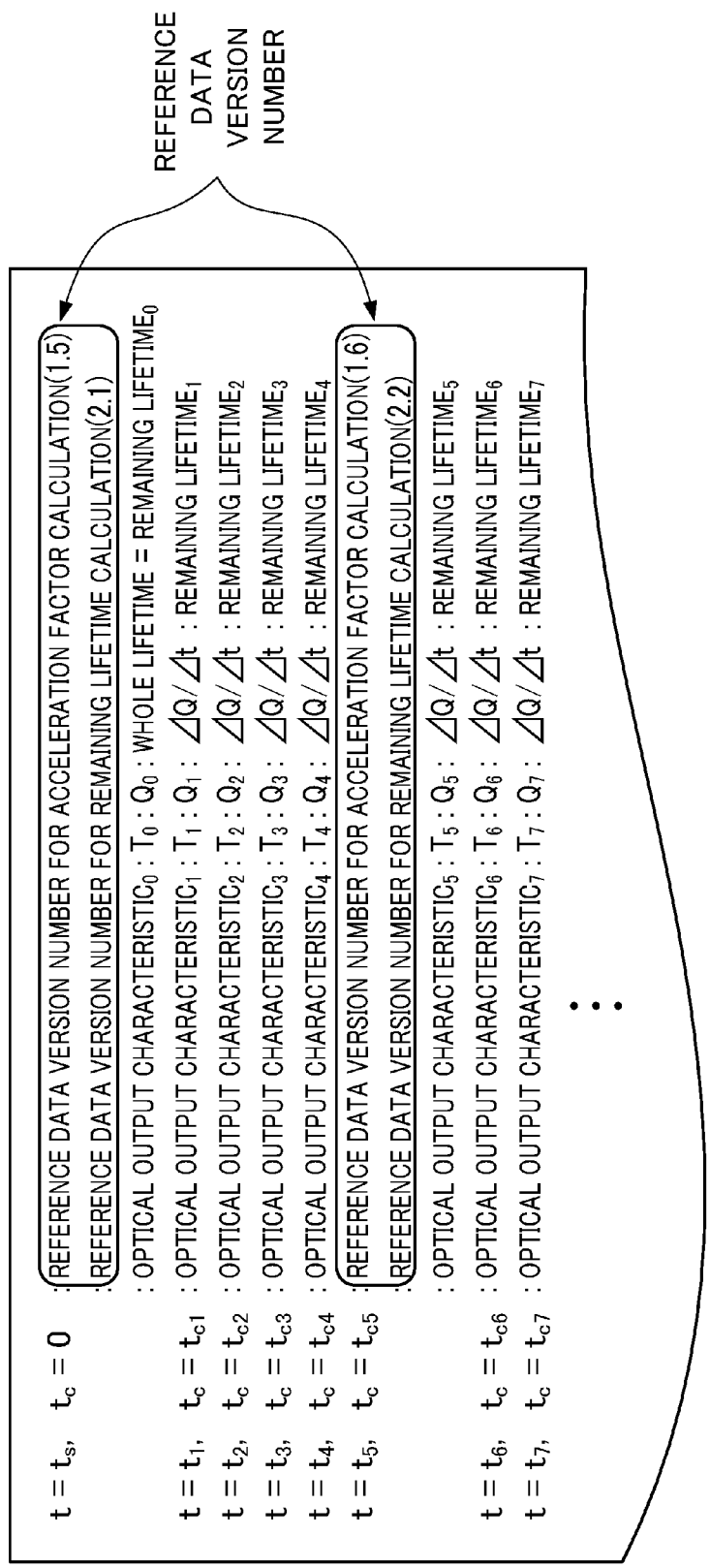
FIG. 11 is a schematic view of an organizational example of data recorded in a recording unit of a laser apparatus according to an eleventh embodiment of the present invention.

By replacing data referenced by the first calculation unit 6 or second calculation unit 9 upon calculation with the latest version, it is possible to improve the calculation accuracy of the effective cumulative driving time $t_c$, whole lifetime $\tau_L$, and remaining lifetime $\tau_R$ after replacement. Even if updating the data to be referenced in the middle of the effective cumulative driving time $t_c$ elapsing, the data recorded in the recording unit 8 of the laser apparatus 1 produced by updating the data referenced in the middle of use can also be used as data for updating the data referenced by the first calculation unit 6 or second calculation unit 9 upon calculation, by leaving as a recording which version of the data was referenced to perform calculation. FIG. 11 schematically shows an organizational example of data recorded in the recording unit 8. In the case of including data to be referenced inside the laser apparatus 1, it may be configured so that substitution of data to be referenced is performed automatically by capturing data outputted from a server or the like of a fog computing system conducting the collection or analysis of the aforementioned data through a network.

Twelfth Embodiment

In a laser apparatus according to a twelfth embodiment of the present invention, the first calculation unit 6 can calculate the acceleration factor F (P,T) as a product of a first acceleration factor $F_P$ (P) depending on the optical output from the light source 2 or at least one drive condition value P of the light source 2 deciding the optical output, and a second acceleration factor $F_T$ (T) depending on the temperature $T_M$ detected by the temperature detection unit 5, or the temperature $T_L$ of the light source 2 obtained from the temperature $T_M$ detected by the temperature detection unit 5, i.e. $F_P$ (P)×$F_T$ (T).

Figure 12:
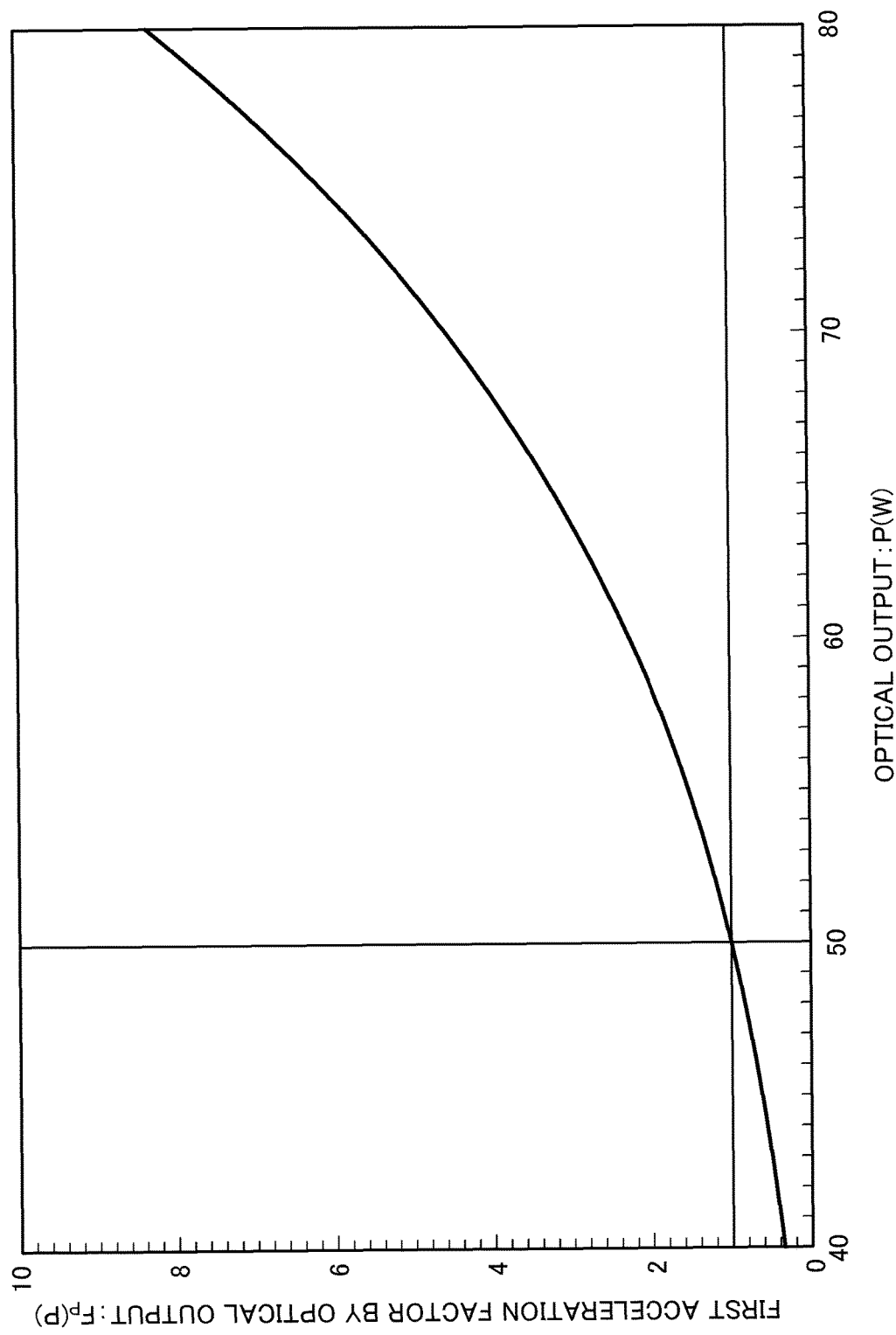
FIG. 12 is an example of data (graph) referenced upon a first calculation unit calculating a first acceleration factor by optical output, which is a drive condition value, in a laser apparatus according to a twelfth embodiment of the present invention.
Figure 13:
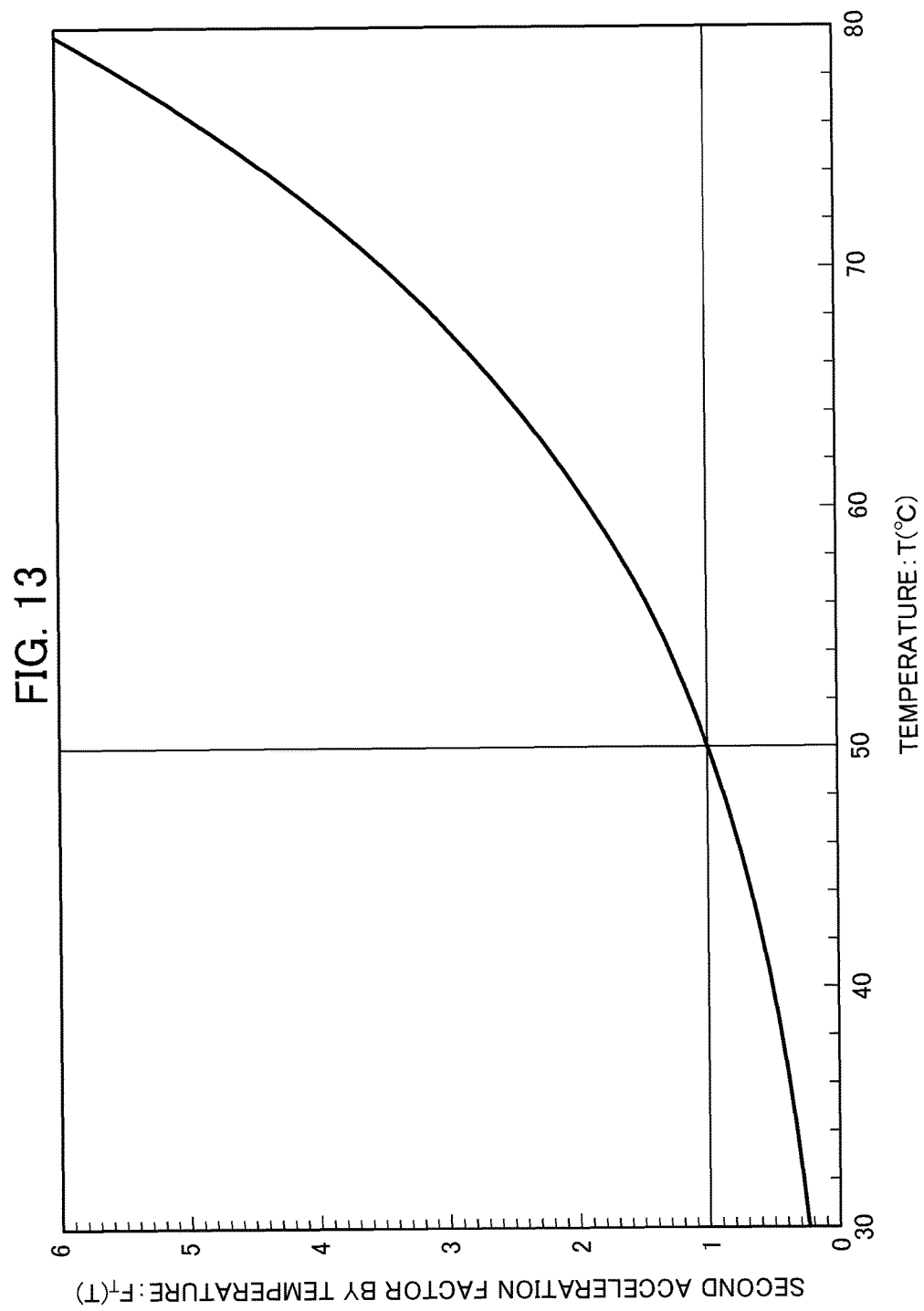
FIG. 13 is an example of data (graph) referenced upon the first calculation unit calculating a second acceleration factor by temperature, in the laser apparatus according to the twelfth embodiment of the present invention.

The data referenced by the first calculation unit upon calculating the acceleration factor can calculate the acceleration factor F (P,T)=$F_P$ (P)×$F_T$ (T) by referencing not a two-dimensional data table giving the acceleration factor F (P,T) relative to the two parameters of the drive condition value P and temperature T as shown in FIG. 2, but rather a graph showing the relationship of the drive condition value P with the first acceleration factor $F_P$ (P) such as that shown in the example of FIG. 12, and a graph showing the relationship of the temperature T with the second acceleration factor $F_T$ (T) such as that shown in the example of FIG. 13. In FIG. 12, the optical output from the light source 2 or at least one drive condition value P of the light source 2 that decides the optical output is defined as the optical output, and the standard condition value Ps is 50 W. The drive condition value P can be set as the driving current or the like, other than the optical output. In addition, the standard temperature $T_S$ is 50° C. in FIG. 13. In other words, in the examples shown in FIGS. 12 and 13, a case of the optical output being 50 W, and the temperature $T_M$ detected by the temperature detection unit 5 or temperature $T_L$ of the light source 2 obtained from the temperature $T_M$ detected by the temperature detection unit 5 is the standard drive condition, and the acceleration factor F (50 W, 50° C.) equals $F_P$ (50 W)×$F_T$ (50° C.)=1.

In a case of the data to be referenced being a two-dimensional data table, the data volume required to be acquired from the past results data is large, and time is required in data acquisition; however, if expressing the acceleration factor F (P,T) by the product of the first acceleration factor $F_P$ (P) depending on the drive condition value P and the second acceleration $F_T$ (T) depending on the temperature T, it is possible to drastically reduce the data to be acquired, and thus possible to create the required data to be referenced in comparatively few man-hours.

Thirteenth Embodiment

In a laser apparatus according to a thirteenth embodiment of the present invention, the first acceleration factor $F_P$ (P) is an acceleration factor at a condition fixing the temperature of the light source 2 to the standard temperature $T_S$, for which the acceleration effect on lifetime consumption caused by the temperature of the light source 2 changing by the generated heat amount of the light source 2 changing concomitant with the drive condition value P changing is excluded, and the second acceleration factor $F_T$ (T) is an acceleration factor by the temperature of the light source 2.

For example, in the case of the drive condition value P giving the acceleration factor F (P,T) being the driving current, since the first acceleration factor $F_P$ (P) by the driving current will differ in accordance with the temperature, data for calculating each first acceleration factor $F_P$ (P) relative to a plurality of temperatures is required for each; however, when detaching the influence on the acceleration of lifetime consumption due the change in temperature accompanying the change in drive condition, there is no need to provide data of acceleration factors by the driving current relative to a plurality of temperatures, and thus it is possible to further reduce the required data volume.

In order to establish the first acceleration factor $F_P$ (P) as an acceleration factor not depending on temperature, it is necessary to exclude the acceleration effect on lifetime consumption caused by the temperature of the light source 2 changing from the generated heat amount of the light source 2 changing concomitant with the drive condition value P changing, and thus it is necessary to establish an acceleration factor with a condition fixing the temperature of the light source 2 at the standard temperature $T_S$, and for the second acceleration factor $F_T$ (T) to define the acceleration factor by the temperature of the light source 2.

Figure 14:
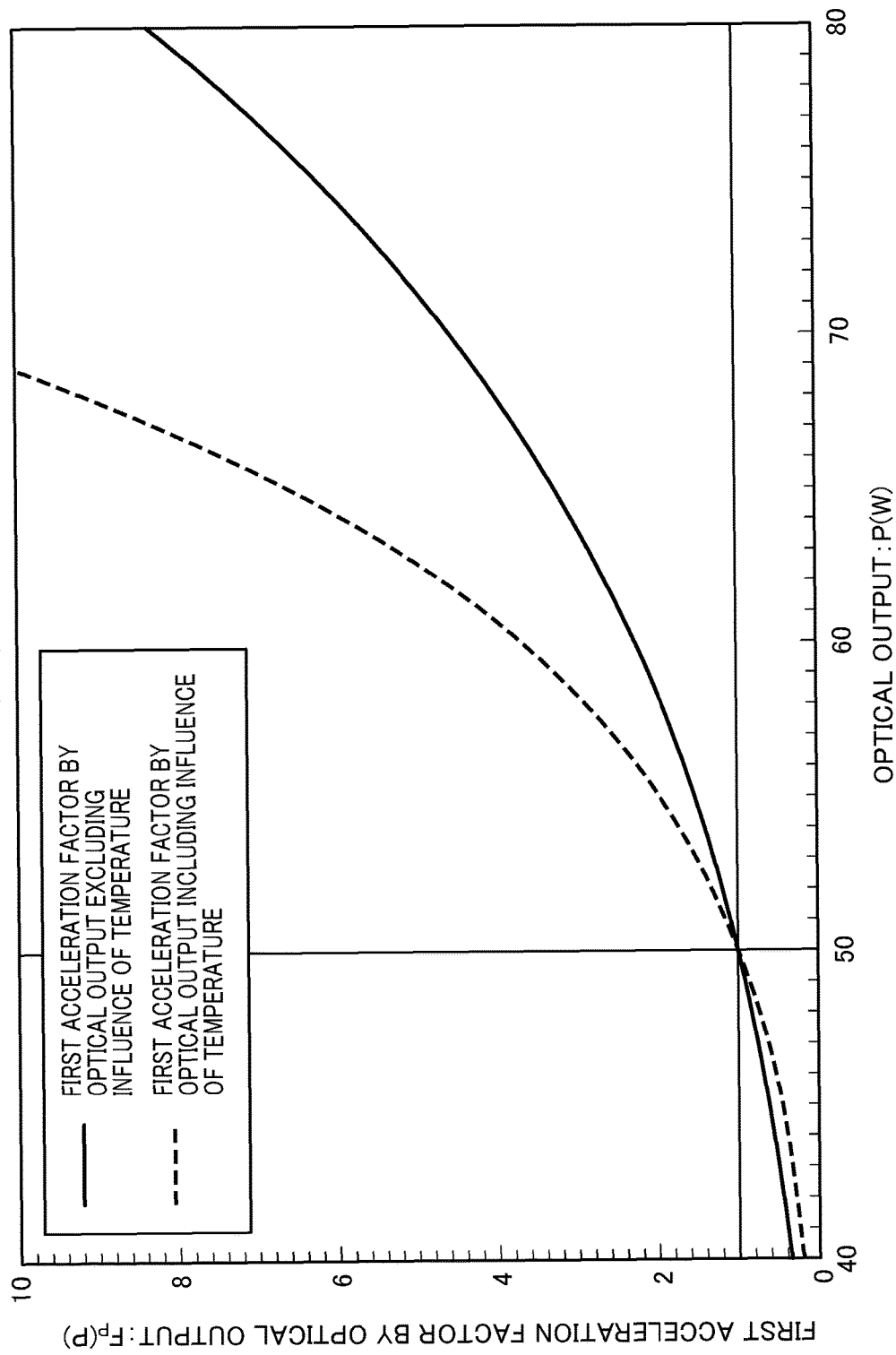
FIG. 14 is an example of data (graph) referenced upon a first calculation unit calculating a first acceleration factor by optical output, which is a drive condition value, in a laser apparatus according to a thirteenth embodiment of the present invention.

For cases of the drive condition value P giving the acceleration factor being the optical output, for example, FIG. 14 exemplifies the acceleration factor by the optical output in a case of fixing the temperature of the cooling unit 12 to a certain temperature, and the acceleration factor by the optical output in a case of fixing the temperature of the light source 2 to the standard temperature. For the former, since there is thermal resistance between the light source 2 and the cooling unit 12, the temperature of the light source 2 rises along with an increase in optical output; therefore, it is the first acceleration factor $F_P$ (P) by the optical output including the influence of temperature, and the latter is a first acceleration factor $F_P$ (P) by the optical output excluding the influence of temperature. Since the first acceleration factor $F_P$ (P) changes even at the same optical output when the temperature of the cooling unit 12 changes, for the former, a plurality of graphs is necessary so that the first acceleration factor $F_P$ (P) is obtained for a plurality of temperatures of the cooling unit 12; however, for the latter, the first acceleration factor $F_P$ (P) can be derived by simply referencing one graph, even if the temperature of the cooling unit 12 changes.

Fourteenth Embodiment

Figure 15:
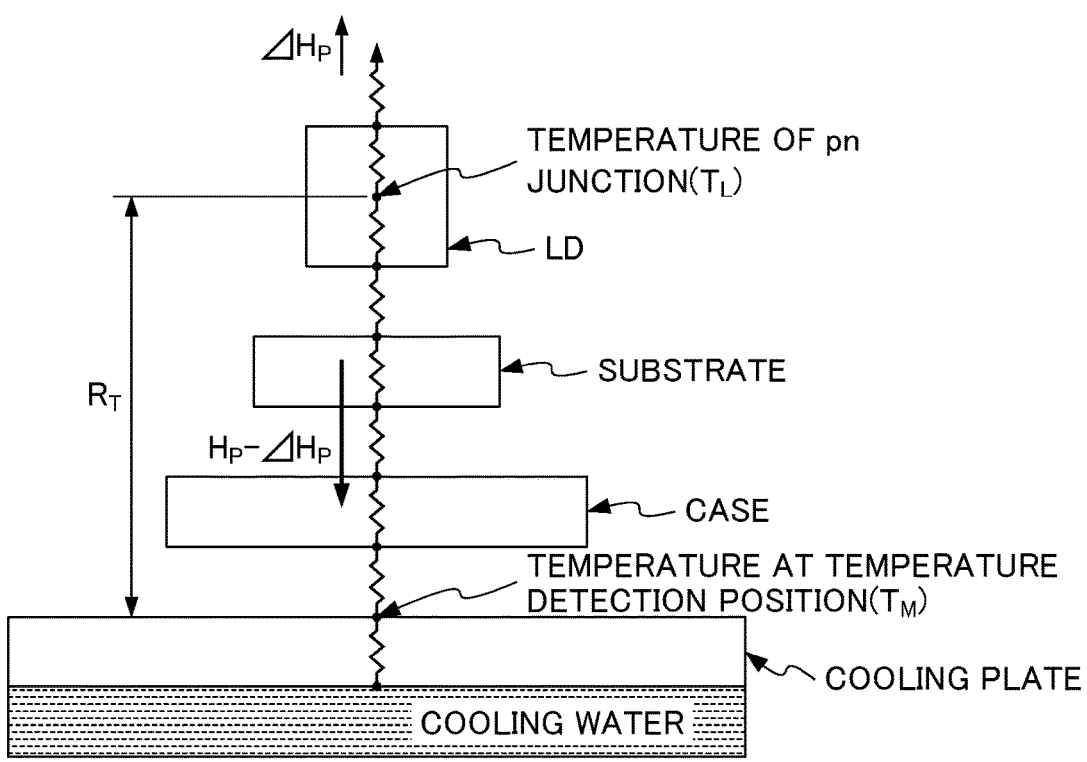
FIG. 15 is a drawing schematically showing the flow of heat, etc. in order to explain a method of deriving the temperature of a pn junction, in a laser apparatus according to a fourteenth embodiment of the present invention.

In a laser apparatus according to a fourteenth embodiment of the present invention, the light source 2 is a laser diode or a laser diode module configured from a plurality of laser diodes, the temperature detection unit 5 is installed so as to detect the temperature of any thermal path from the pn junction of the laser diode until the cooling unit 12 that absorbs the heat generated at the pn junction, as shown in FIG. 15, and the first calculation unit 6 can calculate a second acceleration factor $F_T$ (T) relative to the temperature $T_L$ of the pn junction calculated by the formula $T_L = T_M + R_t \cdot (H_P - \Delta H_P) \approx T_M + R_t \cdot H_P$, from the temperature $T_M$ detected by the temperature detection unit 5, thermal resistance $R_t$ from the temperature detection position until the pn junction, and the heat generation amount $H_P$ of the pn junction calculated from the optical output characteristic of the light source 2. The heat generation amount $\Delta H_P$ not passing through the thermal path from the pn junction until the cooling unit 12 absorbing the heat generated by the pn junction is normally $\Delta H_P < H_P$; therefore, it is ignored in the above-mentioned formula.

The above-mentioned thermal resistance $R_t$ can be estimated from the heat generation amount at the pn junction, shift amount in laser wavelength, temperature $T_M$ detected by the temperature detection unit, etc., and once estimated, even if using the same values, the error will be small and not a problem in laser diodes of the same design specification. In addition, the heat generation amount $H_P$ can be calculated by the formula of heat generation=applied voltage×driving current−optical output energy, if the applied voltage to the light source 2, i.e. laser diode, is known for the optical output characteristic of the laser diode. It is desirable to measure and record the applied voltage to the light source together with the driving current as optical output characteristic data in the optical output characteristic recorded in the recording unit 8 so that the heat generation amount of the light source 2 is known.

If the temperature of the pn junction, which is the temperature $T_L$ of the light source 2, is known in the above way, the second acceleration factor $F_T$ ($T_L$), which is the acceleration factor by the temperature $T_L$ of the pn junction can be calculated using the Arrhenius model equation of Formula 3, which is widely used in accelerated life testing, etc.

[Math. 2]

$$F_T(T_L) = \exp\left(-\frac{E_a}{k_B \cdot T_L}\right) \Big/ \exp\left(-\frac{E_a}{k_B \cdot T_S}\right) \quad \text{(Formula 3)}$$

In Formula 3, $E_a$ is the activation energy (eV), and $k_B$ is Boltzmann's constant=8.6173×10$^{-5}$ (eV/K). $T_L$ is the temperature of the light source 2, and is the temperature of the pn junction in the case of the light source 2 being a laser diode, and $T_S$ is the standard temperature as mentioned above. It is necessary to use the temperature expressed by absolute temperature in Formula 3. When using the Arrhenius model equation, the second acceleration factor $F_T$ (T) can be calculated by simply obtaining the activation energy $E_a$.

When using the second acceleration factor $F_T (T_L)$ related to the temperature $T_L$ of the light source 2, i.e. pn junction of the laser diode, since it is possible to exclude the influence on acceleration by the temperature T from the acceleration factor by the drive condition value P other than temperature such as the driving current and the optical output, it is unnecessary to include graphs of the first acceleration factor $F_P$ (P) relative to a plurality of temperatures as in FIG. 12, and the number of data sets required to calculate the first acceleration factor $F_P$ (P) is small, and thus the time needed in data acquisition can be drastically reduced.

It should be noted that, in the case of the light source 2 being a laser diode or a laser diode module configured from a plurality of laser diodes, the plurality of laser diodes or laser diode module is often mounted to a cooling plate for absorbing the heat generated by the laser diodes, either directly or via a storage case; however, in order to measure the temperature distribution of the cooling plate, a plurality of the temperature detection units 5 may be installed in a state thermally connected to the cooling plate, and finer lifetime control may be performed such as by calculating the different effective cumulative driving times $t_c$ according to the position of the laser diode on the cooling plate. In the case of the plurality of laser diodes being divided into a plurality of groups that can be driven independently, it is possible to reference the remaining lifetime $\tau_R$ of each group, and level the remaining lifetime $\tau_R$ by preferentially driving the laser diodes of the group having a long remaining lifetime $\tau_R$.

In addition, by constructing a heat pipe in the cooling plate to configure so that the temperature distribution of the cooling plate becomes uniform, it is possible to avoid a situation in which the effective cumulative driving time $t_c$ of a specific laser diode is drastically larger than another laser diode, and the lifetime is exhausted considerably earlier than the other laser diode.

Fifteenth Embodiment

In a laser apparatus according to a fifteenth embodiment of the present invention, the light source 2 is a laser diode or a laser diode module configured from a plurality of laser diodes, and the first calculation unit 6 can calculate the first acceleration factor $F_P$ (P) as a power function of an equation arrived at by dividing the drive condition value P by the standard drive condition value Ps, or an equation arrived at by dividing a value produced by subtracting a certain positive integer from the drive condition value P, by a value arrived at by subtracting the certain positive integer from the standard drive condition value $P_S$, as shown in Formulas 4 and 5.

[Math. 3]

$$F_P (P) = (P/P_S)^n \quad \text{(Formula 4)}$$

$$F_P (P) = ((P-\epsilon)/(P_S-\epsilon))^n \quad \text{(Formula 5)}$$

Herein, $P_S$ is the standard drive condition value, and $\epsilon$ is a positive integer.

Figure 16:
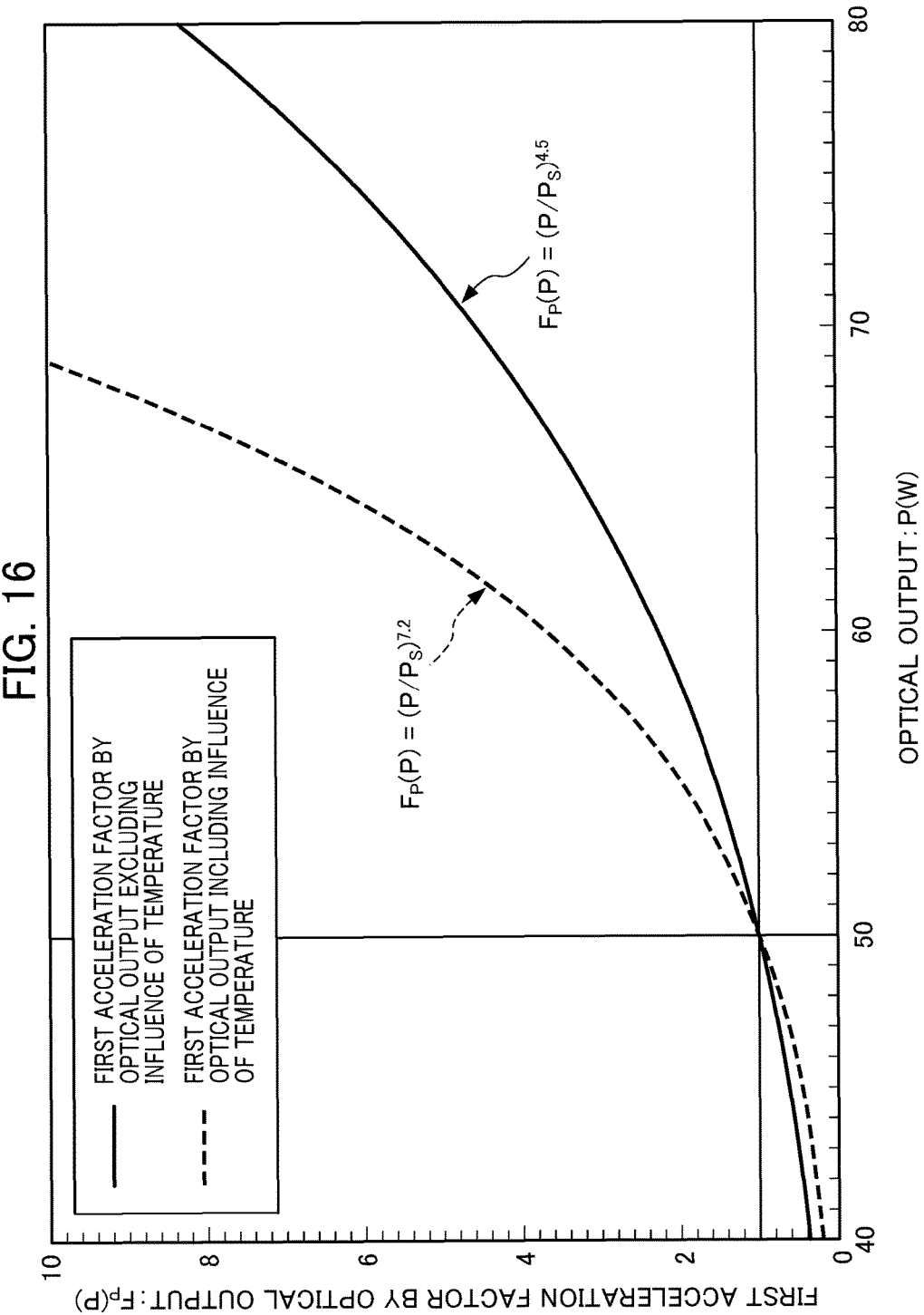
FIG. 16 is an example of data (graph) referenced upon a first calculation unit calculating a first acceleration factor by optical output, which is a drive condition value, in a laser apparatus according to a fifteenth embodiment of the present invention.
Figure 17:
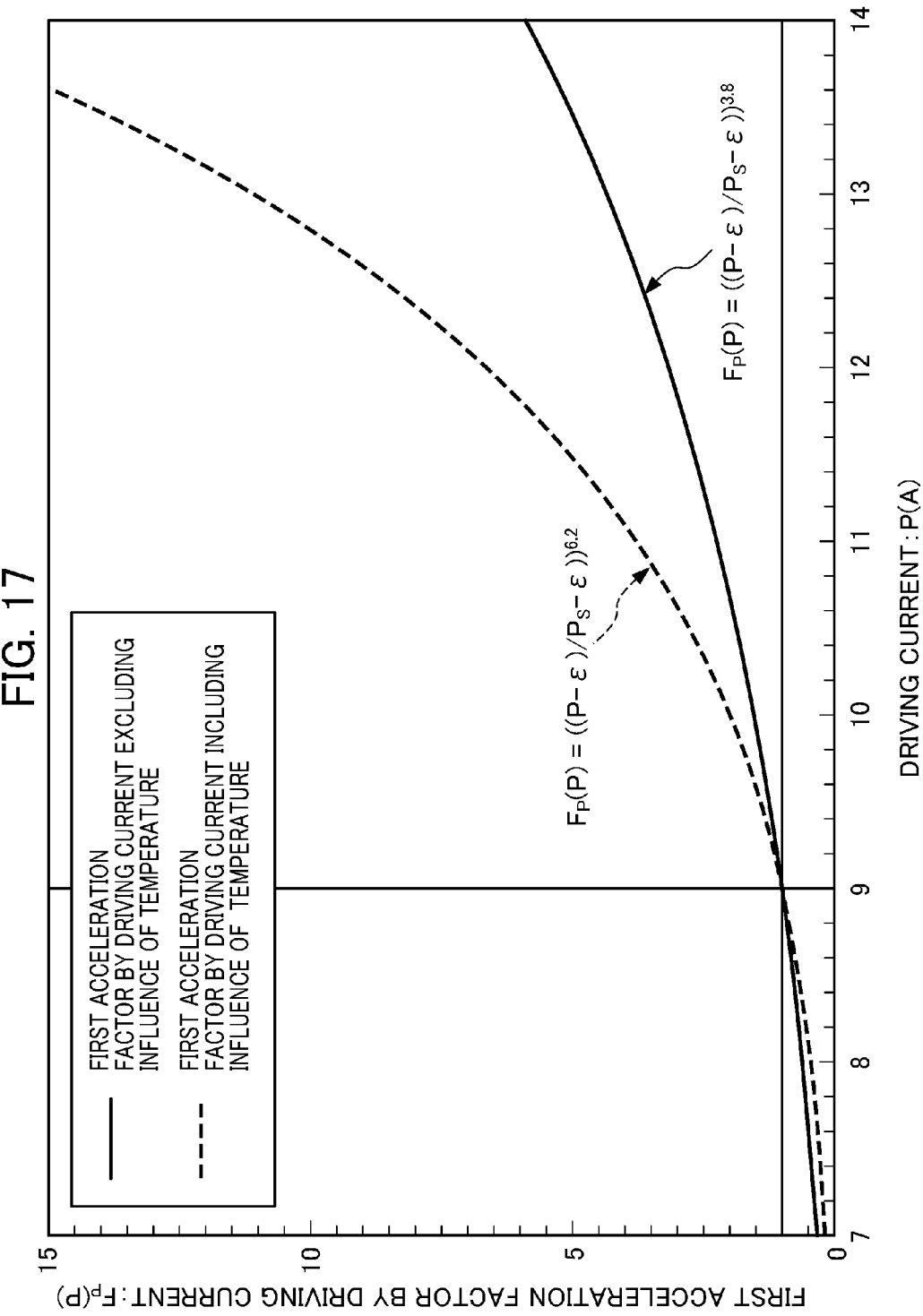
FIG. 17 is an example of data (graph) referenced upon the first calculation unit calculating the first acceleration factor by driving current, which is a drive condition value, in the laser apparatus according to the fifteenth embodiment of the present invention.

FIG. 16 is a case of the optical output or at least one drive condition value P of the light source 2 that decides the optical output being the optical output, and the first acceleration factor $F_P$ (P) is calculated by Formula 4, in which the standard drive condition value $P_S$ (standard optical output) is 50 W. FIG. 17 is a case of the drive condition value P being the driving current, and the first acceleration factor $F_P$ (P) is calculated by Formula 5, in which $\epsilon$ corresponds to an approximate threshold current, and the standard drive condition value $P_S$ (standard driving current) is 9 A.

The first acceleration factor $F_P$ (P) by a drive condition value other than temperature is also derived by a formula such as that shown in FIG. 14 or 15, whereby the data referenced upon calculation of the first acceleration factor $F_P$ (P) is mostly only the exponent n, and the time required in data acquisition is drastically reduced.

For the drive condition value P for which the temperature of the pn junction changes as in optical output or driving current, by using a formula eliminating the influence of temperature accompanying the change in drive condition value P, even if the temperature changes, the first acceleration factor $F_P$ (P) can be calculated with the same formula; therefore, the reference data required upon calculation of the first acceleration factor $F_P$ (P) can be further decreased.

It should be noted that, also for the graph (data) referenced upon calculation of the first acceleration factor $F_P$ (P) such as that shown in FIG. 16 or 17, it may be configured to include a plurality of data sets corresponding to a plurality of effective cumulative driving times $t_c$ as in FIG. 4, so that the first acceleration factor $F_P$ (P) can be calculated with good accuracy, even in a case of the first acceleration factor $F_P$ (P) changing, i.e. exponent n changing, accompanying the elapse of the effective cumulative driving time $t_c$.

Although first to fifteenth embodiments of the present invention have been explained above, the present invention is not to be limited to the aforementioned embodiments. In addition, the effects described in the first to fifteenth embodiments are merely listing the most preferred effects produced from the present invention, and the effects according to the present invention are not to be limited to those described in the first to fifteenth embodiments.

It should be noted that, although the present disclosure describes the laser apparatus 1 as including the first calculation unit 6, second calculation unit 8, recording unit 8, computation unit 7 and control unit 10, it is simply describing by dividing into functional blocks in order to explain the respective functions, and there is no necessity to physically separate from each other, and a plurality of functional blocks among these functional blocks, or all of these functional blocks may be realized by one processor.

The processing of the first calculation unit 6, second calculation unit 9, recording unit 8, computation unit 7 and control unit 10 may be realized by hardware or software. In the case of being realized by software, the programs constituting this software are installed to a computer. In addition, these programs may be distributed to users by recording on removable media, or may be distributed by being downloaded to the computer of the user via the network. Furthermore, these programs may be provided to the computer of the user as a Web service via the network, without being downloaded.

EXPLANATION OF REFERENCE NUMERALS 1 laser apparatus
2 light source
3 power supply unit 4 optical output detection unit
5 temperature detection unit
6 first calculation unit
7 computation unit
8 recording unit
9 second calculation unit
10 control unit
11 laser optical system
12 cooling unit
13 input unit
14 display unit

What is claimed is:

1. A laser apparatus comprising:
at least one light source that functions as a laser beam source or excitation light source;
at least one power supply unit that supplies driving current to the light source;
at least one optical output detection unit that detects optical output from the light source;
at least one temperature detection unit that detects temperature of the light source or a member that is thermally connected with the light source;
a first calculation unit that defines, as a standard, a case of a temperature detected by the temperature detection unit or the temperature of the light source obtained from the temperature detected by the temperature detection unit being a standard temperature, and optical output from the light source or at least one drive condition value of the light source deciding the optical output being a standard condition value, and calculates an acceleration factor of lifetime consumption of the light source which depends on the temperature and the drive condition value;
a second calculation unit that calculates at least one lifetime among a whole lifetime of the light source and a remaining lifetime of the light source relative to at least one characteristic of the light source, among at least one performance index of the light source that changes accompanying driving of the light source and can be obtained from an optical output characteristic of the light source, and a change rate of the performance index;
a computation unit that computes a time integral of the acceleration factor as an effective driving time of the light source;
a recording unit that records the time integral of the acceleration factor from a certain setting time until an arbitrary time that is later than the setting time, which was computed by the computation unit, as an effective cumulative driving time until the arbitrary time,
and can record the whole lifetime and the remaining lifetime calculated by the second calculation unit with the optical output characteristic; and
a control unit that controls each of the units.

2. The laser apparatus according to claim 1, wherein the acceleration factor calculated by the first calculation unit is dependent on the effective cumulative driving time.

3. The laser apparatus according to claim 1, wherein the second calculation unit has a function of calculating a remaining lifetime of the light source at the arbitrary time by subtracting the effective cumulative driving time until the arbitrary time recorded in the recording unit from a whole lifetime of the light source calculated relative to at least one characteristic of the light source among the performance index of the light source and a change rate of the performance index.

4. The laser apparatus according to claims 1, wherein the power supply unit outputs driving current for optical output measurement to the light source according to a command from the control unit following a predetermined schedule, the control unit measures an optical output characteristic of the light source expressing a relationship between the driving current and optical output detected by the optical output detection unit, and the recording unit has a function of adding or recording the optical output characteristic in the recording unit to be associated with the effective cumulative driving time at a corresponding time.

5. The laser apparatus according to claims 1, comprising a plurality of the light sources for which the driving current is independently controllable, and comprising at least one of the optical output detection units capable of detecting optical output relative to each of the light sources for which the driving current is independently controllable.

6. The laser apparatus according to claims 1, wherein the remaining lifetime of the light source calculated relative to the performance index of the light source and a change rate of the performance index by the second calculation unit is also dependent on the effective cumulative driving time.

7. The laser apparatus according to claims 1, wherein the laser apparatus has a function of, in a case of the change rate or a variation range of the performance index obtained from the optical output characteristic recorded or added in the recording unit to be associated with the effective cumulative driving time exceeding a predetermined value that exceeds measurement error for the optical output characteristic, replacing the whole lifetime calculated by the second calculation unit based on the performance index of the light source or the change rate of the performance index, with a value arrived at by adding the effective cumulative driving time to the remaining lifetime of the light source calculated from the performance index of the light source obtained from the optical output characteristic of the light source newly measured and the change rate of the performance index.

8. The laser apparatus according to claims 1, wherein the recording unit has a function of recording or adding the remaining lifetime of the light source at the effective cumulative driving time, calculated by the second calculation unit, along with the optical output characteristic recorded or added to be associated with the effective cumulative driving time, in the recording unit.

9. The laser apparatus according to claims 1, wherein the recording unit has a function of recording or adding information related to at least one drive condition of the light source among a temperature detected by the temperature detection unit or the temperature of the light source obtained from the temperature detected by the temperature detection unit, and the drive condition value of the light source, over a time period from a measurement time of the optical output characteristic until a subsequent measurement time of the optical output characteristic, together with the optical output characteristic recorded or added to be associated with the effective cumulative driving time in the recording unit.

10. The laser apparatus according to claims 1, wherein data recorded in the recording unit can be outputted by a recording medium or by a communication means.

11. The laser apparatus according to claims 1, wherein at least one set of data among data referenced by the first calculation unit upon calculation of the acceleration factor and data referenced by the second calculation unit upon calculating the whole lifetime or the remaining lifetime of the light source can be substituted for data by way of a recording medium or communication means, at a moment at which the effective cumulative driving time of the laser apparatus elapses, and a recording can be left in the recording unit of at which moment of the effective cumulative driving time the data to be referenced was substituted.

12. The laser apparatus according to claims 1, wherein the first calculation unit calculates the acceleration factor as a product of a first acceleration factor depending on optical output from the light source or at least one drive condition value of the light source deciding the optical output, and a second acceleration factor depending on temperature detected by the temperature detection unit or a temperature of the light source obtained from the temperature detected by the temperature detection unit.

13. The laser apparatus according to claim 12, wherein the first acceleration factor is an acceleration factor at a condition fixing the temperature of the light source to the standard temperature, at which an acceleration effect on lifetime consumption caused by the temperature of the light source changing due to heat generation amount of the light source changing concomitant with the drive condition value changing is excluded; and the second acceleration factor is an acceleration factor according to the temperature of the light source.

14. The laser apparatus according to claim 12, wherein the light source is a laser diode or a laser diode module configured from a plurality of laser diodes, wherein the temperature detection unit is installed so as to detect temperature at any position on a thermal path from a pn junction of the laser diode until a cooling unit absorbing heat generated by the pn junction, and wherein the first calculation unit calculates the second acceleration factor relative to the temperature of the pn junction which is calculated from the temperature detected by the temperature detection unit, thermal resistance from a temperature detection position until the pn junction, and a heat generation amount of the pn junction calculated from an optical output characteristic of the light source.

15. The laser apparatus according to claims 12, wherein the light source is a laser diode or a laser diode module configured from a plurality of laser diodes, and wherein the first calculation unit calculates the first acceleration factor as an power function of an equation arrived at by dividing the drive condition value by a standard drive condition value, or an equation arrived at by dividing a value arrived at by subtracting a certain positive integer from the drive condition value, by a value arrived at by subtracting the certain positive integral from the standard drive condition value.

\* \* \* \* \*